United States Patent
Angehrn et al.

Patent Number: 5,939,410
Date of Patent: Aug. 17, 1999

[54] 1-CARBA-(DETHIA)-CEPHALOSPORIN DERIVATIVES

[75] Inventors: Peter Angehrn, Böckten; Paul Hebeisen, Basel, both of Switzerland; Ingrid Heinze-Krauss, Schliengen, Germany; Malcolm Page, Basel, Switzerland

[73] Assignee: Hoffmann-La Roche Inc., Nutley, N.J.

[21] Appl. No.: 08/929,248

[22] Filed: Sep. 10, 1997

[30] Foreign Application Priority Data

Sep. 23, 1996 [EP] European Pat. Off. ............ 96115210

[51] Int. Cl.$^6$ ............... A61K 31/435; C07D 463/00
[52] U.S. Cl. ............................... 514/210; 540/205
[58] Field of Search .............. 540/205; 514/210

[56] References Cited

FOREIGN PATENT DOCUMENTS

| | | |
|---|---|---|
| 0 112 481 | 4/1983 | European Pat. Off. |
| 0 620 225 | 3/1994 | European Pat. Off. |
| 0 761 673 | 3/1997 | European Pat. Off. |
| 94/00457 | 1/1994 | WIPO |
| 96/26943 | 9/1996 | WIPO |

OTHER PUBLICATIONS

Heinze–Krauss, et al., *J. Med. Chem.*, 39(9):1864–1871 (1996).
Ochial, et al., Chemical Abstracts, 95(19), Abstract No. 69101f (1981).
Patent Abstracts of Japan, 4(186) (1980) for JP 55–124790.

*Primary Examiner*—Mark L. Berch
*Attorney, Agent, or Firm*—George W. Johnston; Patricia S. Rocha-Tramaloni; Alan P. Kass

[57] ABSTRACT

Compounds of formula I

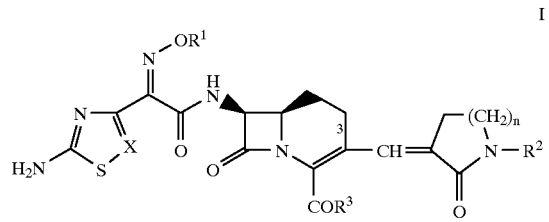

wherein $R^1$ is hydrogen, lower alkyl which is unsubstituted or substituted by fluoro, aralkyl, cycloalkyl, —$COR^4$ or —$C(R^5R^6)CO_2R^7$ —$C(R^5R^6)CONHR^7$; where $R^5$ and $R^6$ are each independently hydrogen or lower alkyl, or $R^5$ and $R^6$ taken together form a cycloalkyl group; $R^4$ is hydrogen or lower alkyl and $R^7$ is hydrogen, lower alkyl, lower alkenyl or a carboxylic acid protecting group;

$R^2$ is hydrogen, hydroxy, lower alkyl-$Q_m$, cycloalkyl, lower alkoxy, lower alkenyl, cycloalkenyl, lower alkynyl, aralkyl-$Q_m$, aryl-$Q_m$, aryloxy, aralkoxy, a heterocyclic ring or heterocyclyl lower alkyl, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, cyano, lower alkyl which is unsubstituted or substituted by fluoro, lower alkoxy, hydroxy, halogen, —$COR^6$, —$C(R^5R^6)CO_2R^7$, —$C(R^5R^6)CONR^5R^8$, —$CONR^5R^6$, —$N(R^6)COOR^{10}$, $R^6OCO$— or $R^6COO$— where $R^5$ and $R^6$ are hydrogen or lower alkyl; $R^7$ is hydrogen, lower alkyl, lower alkenyl or a carboxylic acid protecting group; $R^8$ is hydrogen, lower alkyl or phenyl which is unsubstituted or substituted with at least one halogen, hydroxy, amino, lower alkyl, or lower alkoxy; $R^{10}$ is lower alkyl, lower alkenyl or a carboxylic acid protecting group;

Q is —CHR—, —CO— or —$SO_2$—;

R is hydrogen or lower alkyl;

$R^3$ is hydroxy, —O—, lower alkoxy, —OM and M represents an alkali metal;

m is 0 or 1;

n is 0, 1 or 2;

x is CH or N as well as readily hydrolysable esters thereof, pharmaceutically acceptable salts of said compounds and hydrates of the compounds of formula I and of their esters and salts are provided. These compounds have valuable antiinfective properties.

177 Claims, No Drawings

1-CARBA-(DETHIA)-CEPHALOSPORIN DERIVATIVES

The present invention relates to compounds of formula I

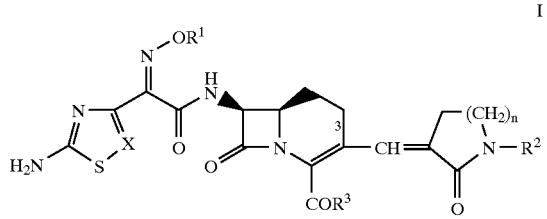

wherein $R^1$ is hydrogen, lower alkyl which is unsubstituted or substituted by fluoro, aralkyl, cycloalkyl, —$COR^4$ or —$C(R^5R^6)CO_2R^7$ —$C(R^5R^6)CONHR^7$; where $R^5$ and $R^6$ are each independently hydrogen or lower alkyl, or $R^5$ and $R^6$ taken together form a cycloalkyl group; $R^4$ is hydrogen or lower alkyl and $R^7$ is hydrogen, lower alkyl, lower alkenyl or a carboxylic acid protecting group;

$R^2$ is hydrogen, hydroxy, lower alkyl-$Q_m$, cycloalkyl, lower alkoxy, lower alkenyl, cycloalkenyl, lower alkynyl, aralkyl-$Q_m$, aryl-$Q_m$, aryloxy, aralkoxy, a heterocyclic ring or heterocyclyl lower alkyl, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, cyano, lower alkyl which is unsubstituted or substituted by fluoro, lower alkoxy, hydroxy, halogen, —$COR^6$, —$C(R^5R^6)CO_2R^7$, —$C(R^5R^6)CONR^5R^8$, —$CONR^5R^6$, —$N(R^6)COOR^{10}$, $R^6OCO$— or $R^6COO$— where $R^5$ and $R^6$ are hydrogen or lower alkyl; $R^7$ is hydrogen, lower alkyl, lower alkenyl or a carboxylic acid protecting group; $R^8$ is hydrogen, lower alkyl or phenyl which is unsubstituted or substituted with at least one halogen, hydroxy, amino, lower alkyl or lower alkoxy; $R^{10}$ is lower alkyl, lower alkenyl or a carboxylic acid protecting group;

Q is —CHR—, —CO— or —$SO_2$—;
R is hydrogen or lower alkyl;
$R^3$ is hydroxy, —O—, lower-alkoxy, —OM and M represents an alkali metal;
m is 0 or 1;
n is 0, 1 or 2;
X is CH or N as well as readily hydrolysable esters thereof, pharmaceutically acceptable salts of said compounds and hydrates of the compounds of formula I and of their esters and salts.

In above compounds of formula I the substituent in position 3 can be present in the E-form formula Ia or in the Z-form formula Ib

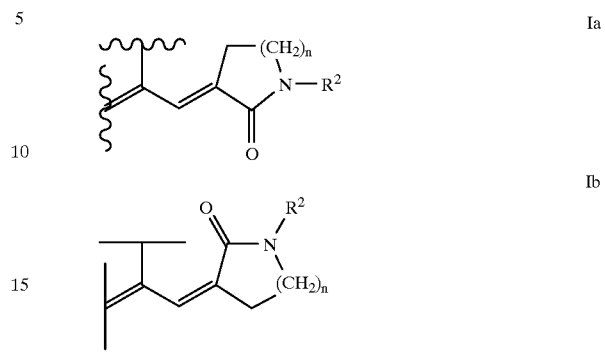

In a particular embodiment of the compounds of formula I n is 1. Moreover $R^1$ is preferably hydrogen, lower alkyl which is unsubstituted or substituted by fluoro, cycloalkyl, —$COR^4$, —$C(R^5R^6)CO_2R^7$ or —$C(R^5R^6)CONHR^7$, especially preferred are compounds of formula I wherein $R^1$ is hydrogen, methyl, cyclopentyl, —$COCH_3$, —$CH_2COOR^7$, —$C(CH_3)_2COOR^7$, or $C(CH_3)_2CONHR^7$ and $R^4$, $R^5$ and $R^6$ are as defined above whereas $R^7$ is hydrogen or t-butyl.

In yet another embodiment of the compounds of formula I $R^2$ is lower alkyl-Q, where Q is —CHR— and R is hydrogen; or $R^2$ is lower alkyl, aryl or a heterocyclic ring, the lower alkyl, cycloalkyl, aryl, and the heterocyclic ring being unsubstituted or substituted with at least one group selected from nitro, lower alkyl which is unsubstituted or substituted by fluoro, hydroxy or halogen.

Especially preferred compounds of formula I are compounds wherein $R^2$ represents a pyridine ring optionally substituted in position 1, for example, pyridine-2-yl, -3-yl or -4-yl, 1-methylpridinium-2-yl, -3-yl or -4-yl, 1-carbamoylmethylpyridinium-2-yl, -3-yl or -4-yl, 1-(N-phenylcarbamoylmethyl)-pyridinium-2-yl, -3-yl or -4-yl, 1-[N-(3-fluoro-4-hydroxyphenyl) carbamoylmethyl)-pyridinium-2-yl, -3-yl or -4-yl, and the like.

The compounds of the formula I are preferably in the Z-form at the oximino group and E-form for the substituent in position 3.

Preferred compounds of formula I include:
(6R, 7S)-7-[(Z)-2-Acetoxyimino-2-(2-amino-thiazolo-4-yl)-acetylamino]-3-[(E)-1-(1-carbamoylmethyl-pyridin-1-ium-3-yl)-2-oxo-pyrrolidin-3-ylidenemethyl]-8-oxo-1-aza-bicyclo[4.2.0]oct-2-ene-2-carboxylate

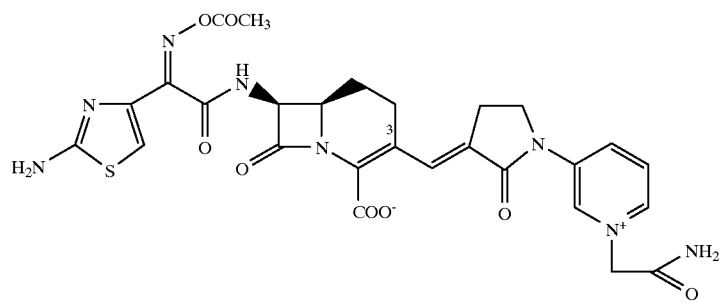

(6R, 7S)-7-[(Z)-2-(2-Amino-thiazol-4-yl)-2-hydroxyimino-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid sodium salt (1:1)

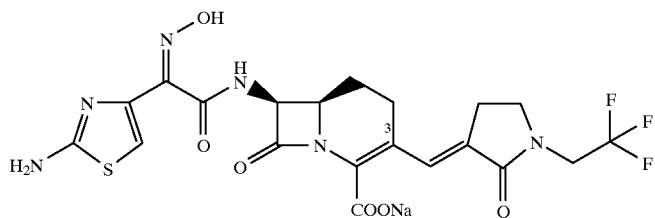

(6R, 7S)-7-[(Z)-2-(Amino-thiazol-4-yl)-2-hydroxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid sodium salt (1:1)

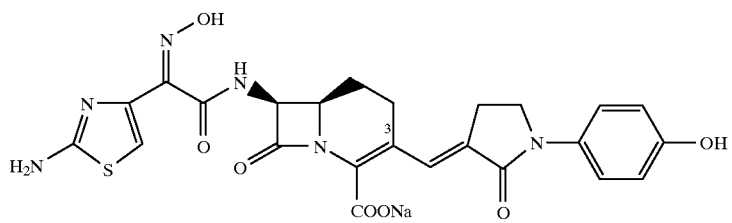

(6R, 7S)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate

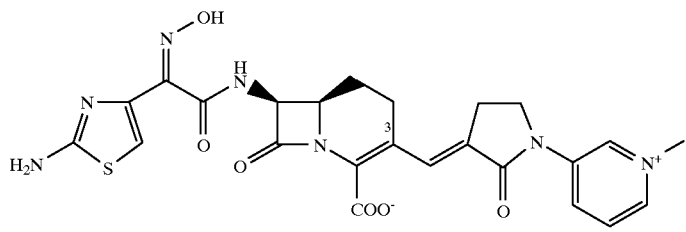

(6R, 7S)-7-[(Z)-2-Acetoxyimino-2-(2-amino-thiazol-4-yl)-acetylamino]-3-(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate

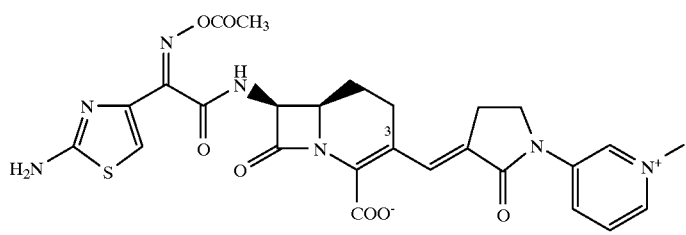

(6R, 7S)-7-[(Z)-2-(2-Amino-thiazol-4-yl)-2-methoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate

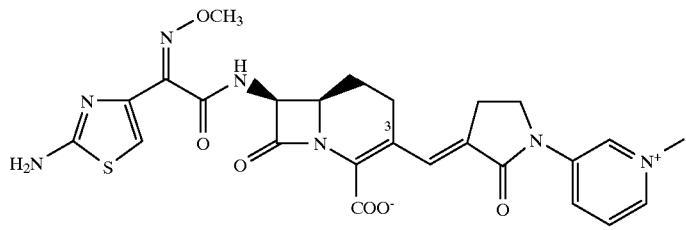

(6R, 7S)-7-[(Z)-2-(2-Amino-thiazol-4-yl)-2-cyclopentyloxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate

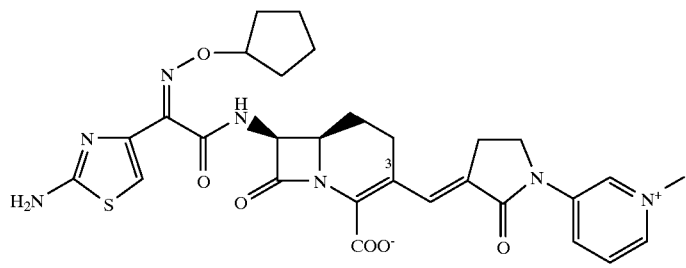

(6R, 7S)-7-[(Z)-2-(5-Amino-[1,2,4]thiadiazol-3-yl)-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate

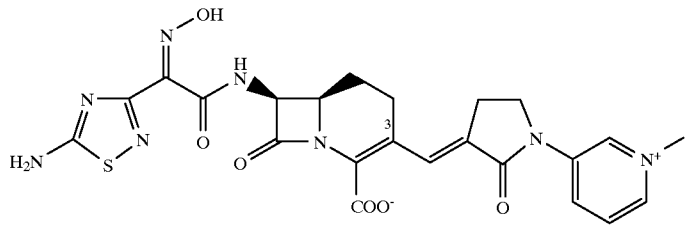

(6R, 7S)-7-[(Z)-2-(5-Amino-[1,2,4]thiadiazol-3-yl)-cyclopentyloximino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate

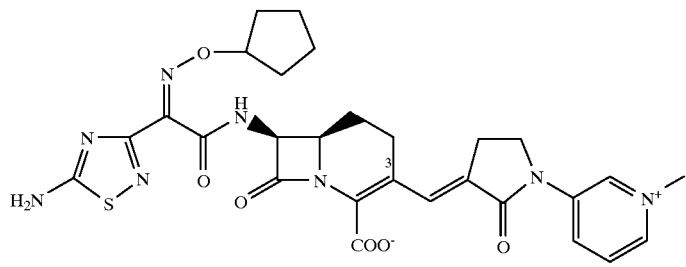

(6R, 7S)-7-[(Z)-2-(2-Amino-thiazol-4-yl)-2-carboxymethoxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate Na salt (1:1)

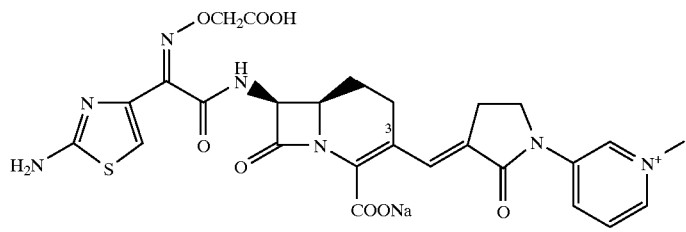

(6R, 7S)-7-[(Z)-2-(2-Amino-thiazol-4-yl)-2-cyclopentyloxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate

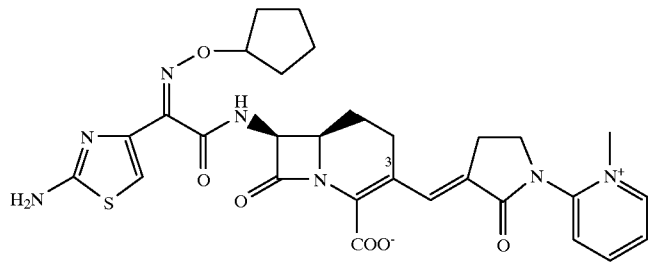

(6R, 7S)-7-[(Z)-2-(2-Amino-thiazol-4-yl)-2-hydroxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate

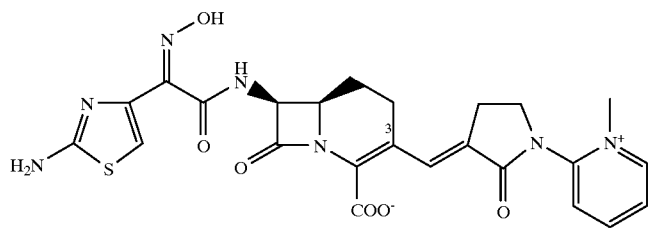

(6R, 7S)-7-[(Z)-2-(2-Amino-thiazol-4-yl)-2-hydroxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate

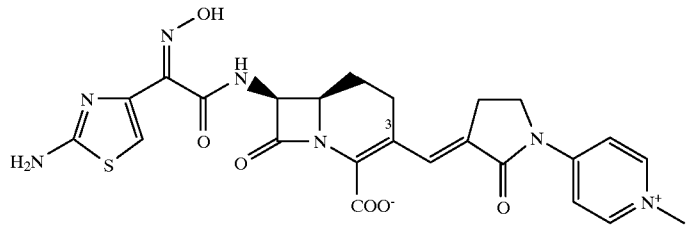

(6R, 7S)-7-[(Z)-2-(2-Amino-thiazol-4-yl)-2-cyclopentyloxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate

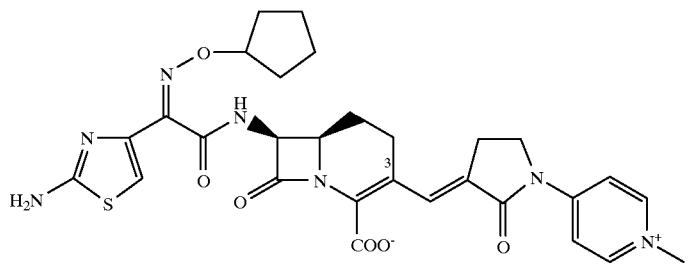

The invention also relates to pharmaceutical compositions and methods of use of the above.

As used herein, the term "lower alkyl unsubstituted or substituted by fluoro" refers to both unsubstituted and fluoro substituted straight and branched chain saturated hydrocarbon groups having 1 to 8 and preferably 1 to 4 carbon atoms, for example, methyl, ethyl, n-propyl, isopropyl, and tertiary butyl. Such groups may be mono or multiply fluoro-substituted as for example fluoromethyl, trifluoromethyl, fluoroethyl, trifluoroethyl and the like.

The term "lower alkoxy" refers to ether groups wherein alkyl is defined as above.

The term "lower alkenyl" refers to unsubstituted or substituted hydrocarbon chain radicals having from 2 to 8 carbon atoms, preferably from 2 to 4 carbon atoms, and having at least one olefinic double bond, e.g. vinyl, allyl, 1-propenyl, 1-, 2- or 3-butenyl etc.

The term "lower alkynyl" refers to unsubstituted or substituted hydrocarbon chain radicals having from 2 to 8 carbon atoms, preferably from 2 to 4 carbon atoms, and having at least one triple bond preferably located at the end of the chain, for example, acetyl?, 2-propynyl, 3-butynyl, etc.

By the term "cycloalkyl" is meant a 3–7 membered saturated carbocyclic moiety, e.g., cyclopropyl, cyclobutyl, cyclopentyl, cyclohexyl, etc.

By the term "cycloalkenyl" is meant a 3–7 membered unsaturated carbocyclic moiety, e.g. cyclopentenyl, cyclohexenyl, etc.

By the term "aralkyl" is meant an alkyl group containing an aryl group. It is a hydrocarbon group having both aromatic and aliphatic structures, that is, a hydrocarbon group in which a lower alkyl hydrogen atom is substituted by a monocyclic aryl group, e.g., phenyl, tolyl, etc.

By the term "aralkoxy" is meant an ether group wherein aralkyl is defined as above.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthryl, phenanthryl, and the like. The aryl group can have at least one substituent selected from, as for example, halogen, hydroxy, cyano, carboxy, nitro, amino, lower alkyl, lower alkoxy, such as in 2,4-difluorophenyl, 4-carboxyphenyl, 4-nitrophenyl, 4-aminophenyl, 4-methoxyphenyl.

By the term "aryloxy" is meant an ether group wherein aryl is defined as above.

By the term "phenyl unsubstituted or substituted with at least one halogen, hydroxy, amino, lower alkyl, or lower alkoxy" is meant phenyl which is unsubstituted, or phenyl substituted with at least one of halogen, hydroxy, amino, lower alkyl or lower alkoxy, for example, phenyl, 3-fluoro-4-hydroxy-phenyl, and the like.

The term "halogen" or "halo" used herein refers to all four forms, that is chlorine or chloro; bromine or bromo; iodine or iodo; and fluorine or fluoro, unless specified otherwise.

As used herein, "heterocyclic ring" refers to an unsaturated or saturated, unsubstituted or substituted 5-, 6-, or 7-membered heterocyclic ring containing at least one hetero atom selected from the group consisting of oxygen, nitrogen, or sulfur. Exemplary heterocyclic rings include, but are not limited to, for example, the following groups: pyridyl, which is optionally substituted in position 1, for example, pyridinium-2-yl, -3-yl or -4-yl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl; thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, 1,6,3,4-dioxadithiopanyl, oxazolidinyl, tetrahydrothienyl, etc. Substituents for the heterocyclic ring include, for example, lower alkyl groups such as methyl, ethyl, propyl, etc., lower alkoxy groups such as methoxy, ethoxy, etc., halogens such as fluorine, chlorine, bromine, etc., halogen substituted alkyl groups such as trifluoromethyl, trichloroethyl, etc., amino, mercapto, hydroxyl, carbamoyl, or carboxyl groups. A further substituent is oxo, such as in 2-oxo-oxazolidin-3-yl, 1,1-dioxo-tetrahydrothien-3-yl. Further examples of substituted heterocycles are 1-methyl-pyridinium-2-yl, -3-yl, -4-yl, 1-ethyl-pyridinium-2-yl, -3-yl, -4-yl, 1-carbamoylmethyl-pyridinium-2-yl, -3-yl, -4-yl, 6-methoxy-pyridin-3-yl, 5-methyl-isoxazol-3-yl, 1-methyl-4-pyridinio.

The term "carboxylic acid protecting group" refers to protecting groups conventionally used to replace the acidic proton of a carboxylic acid. Examples of such groups are benzyhydryl, t-butyl, p-nitrobenzyl, p-methoxybenzyl and allyl.

As used herein pharmaceutically acceptable salts useful in this invention include salts derived from metals, the ammonium salt, quaternary ammonium salts derived from organic bases and amino acid salts. Examples of preferred metal salts are those derived from the alkali metals, for example, lithium ($Li^+$), sodium ($Na^+$) and potassium ($K^+$) are within the scope of this invention. Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like, etc. Those salts derived from amines include salts with N-ethylpiperidine, procaine, dibenzylamine, N,N'-dibenzylethylenediamine, alkylamines or dialkylamines as well as salts with amino acids such as, for example, salts with arginine or lysine. Especially preferred are hydrochlorides, sulfates, phosphates, lactates, mesylates or the inner salt.

As readily hydrolysable esters of the compounds of formula I there are to be understood compounds of formula I, the carboxy group(s) of which (for example, the 2-carboxy group) is/are present in the form of readily hydrolysable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)carbonyl]oxy]ethyl ester; 1-(acetyloxy) ethyl ester; (5-methyl-2-oxo-1,3-dioxol-4-yl) methyl ester; 1-[[(cyclohexyloxy)carbonyl]oxy]ethyl ester; and 3,3-dimethyl-2-oxobutyl ester. It will be appreciated by those of ordinary skill in the art that the readily hydrolysable esters of the compounds of the present invention can be formed at a free carboxy group of the compound, for example, at the carboxy group in position 2 and at a carboxy group —$COOR^7$.

The compounds of formula I as well as their salts and readily hydrolysable esters can be hydrated. The hydration can be effected in the course of making the compounds or can occur gradually as a result of hygroscopic properties of an initially anhydrous product.

The compounds of the present invention are useful as antibiotics having potent and broad antibacterial activity; especially against methicillin-resistent staphylococci (MRSA) and *Pseudomonas aeruginosa*.

The products in accordance with the invention can be used as medicaments, for example, in the form of pharmaceutical preparations for parenteral administration, and for this purpose are preferably made into preparations as lyophilisates or dry powders for dilution with customary agents or pharmaceutically acceptable carriers, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammal, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds of the present invention were tested.

In vitro activity was determined by minimum inhibitory concentration in a microorganism spectrum by the agar dilution method in Mueller Hinton agar, inoculum=$10^4$ CFU/spot.

The following compounds were tested:

A: (6R, 7S)-7-[(Z)-2-(2-Amino-thiazol-4-yl)-2-hydroxyimino-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid sodium salt (1:1)

B: (6R, 7S)-7-[(Z)-2-(Amino-thiazol-4-yl)-2-hydroxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid sodium salt (1:1)

C: (6R, 7S)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate D: (6R, 7S)-7-[(Z)-2-(5-Amino-[1,2,4]thiadiazol-3-yl)-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate E: (6R, 7S)-7-[(Z)-2-(5-Amino-[1,2,4]thiadiazol-3-yl)-cyclopentyloximino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate F: (6R, 7 S)-7-[(Z)-2-(2-Amino-thiazol-4-yl)-2-carboxymethoxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate Na salt (1:1) and G: (6R, 7S)-7-[(Z)-2-(2-Amino-thiazol-4-yl)-2-cyclopentyloxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate The antibacterial Spectrum appears below:
MIC: Minimum Inhibiting Concentration Values

| | Antibacterial Spectrum (MIC, μg/ml) | | | | | | |
|---|---|---|---|---|---|---|---|
| | A | B | C | D | E | F | G |
| S. aureus 6538 | 1 | 1 | 1 | 0.5 | 0.5 | 32 | 2 |
| S. aureus 743 (MRSA) | 32 | 32 | 8 | 8 | 4 | >32 | 32 |
| S. pyogenes b 15 | ≦0.06 | ≦0.06 | ≦0.06 | ≦0.06 | ≦0.06 | 0.12 | ≦0.06 |
| S. pneumoniae. 907 | ≦0.06 | ≦0.06 | ≦0.06 | ≦0.06 | ≦0.06 | ≦0.06 | ≦0.06 |
| E. faecalis 6 | 8 | 4 | 0.5 | 0.25 | 1 | >32 | 1 |
| E. coli 25922 | ≦0.06 | 0.25 | ≦0.06 | 0.06 | ≦0.06 | ≦0.06 | ≦0.06 |
| E. coli TEM1 | 0.12 | 0.12 | ≦0.06 | 0.25 | 1 | ≦0.06 | 0.5 |
| K. pneumoniae 418 | 0.12 | 0.12 | ≦0.06 | ≦0.06 | 0.25 | ≦0.06 | 0.25 |
| S. marcescens 69438 | 2 | 4 | 0.12 | 0.12 | 1 | ≦0.06 | 0.5 |
| E. cloacae 908SSi | 2 | 0.5 | ≦0.06 | 0.12 | ≦0.06 | ≦0.06 | ≦0.06 |
| E. cloacae 908R | >32 | >32 | 2 | 1 | 0.5 | 4 | 2 |
| C. freundii 902 | 0.25 | 0.5 | ≦0.06 | ≦0.06 | ≦0.06 | ≦0.06 | ≦0.06 |
| C. freundii 43 | 8 | 32 | 0.5 | 0.5 | 0.5 | 2 | 1 |
| P. mirabilis 2117 | ≦0.06 | — | ≦0.06 | 0.12 | 2 | ≦0.06 | 1 |
| P. vulgaris 1028 | >32 | >32 | 16 | >32 | 32 | 0.12 | 16 |
| P. aeruginosa ATCC27853 | 32 | 32 | 4 | 8 | 8 | 1 | 4 |

The compounds of the formula I in accordance with the invention as well as their pharmaceutical acceptable salts, hydrates, or readily hydrolyzable esters can be made in accordance with the invention by (a) treating a compound having the formula II

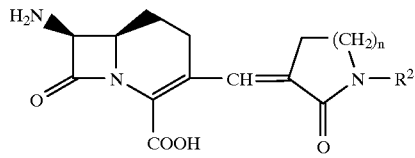

in which $R^2$ and n are defined above, or an ester or salt thereof, with a carboxylic acid of formula III

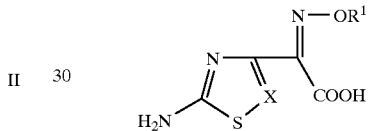

in which $R^1$ and X are defined above, or a reactive functional derivative thereof, or (b) cleaving off the amino, hydroxy and/or carboxy protecting group in a compound having the formula IV

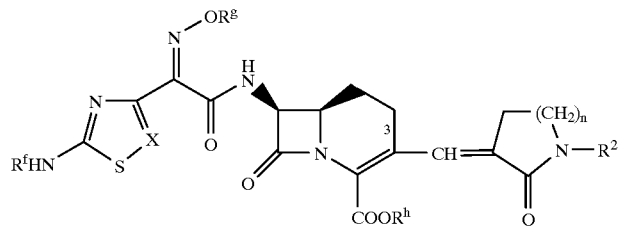

in which $R^2$ is defined above, $R^f$ is hydrogen or an amino protecting group, $R^g$ is hydrogen or a hydroxy protecting group, $R^h$ is hydrogen or a carboxy protecting group, provided that at least one of $R^f$, $R^g$ and $R^h$ is a corresponding protecting group or a salt thereof, or by (c) alkylation of a compound of formula

V

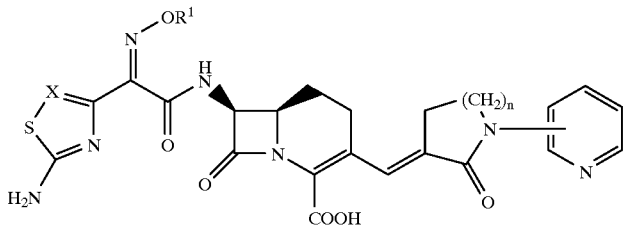

wherein $R^1$, X and n are as defined above,
with a alkylating agent such a methyliodide, dimethylsulfate, trimethyloxonium tetrafluoroborate, bromo- or iodoacetamide, or (d) for making a readily hydrolysable ester of a compound of formula I subjecting a carboxylic acid of formula I to a corresponding esterification, or (e) for making salts or hydrates of a compound of formula I or hydrates of said salts converting a compound of formula I into a salt or hydrate or into a hydrate of said salts.

The reaction of compounds of formula II and III or a reactive derivative of formula III according to embodiment (a) can be carried out in a manner known to those of ordinary skill in the art. The carboxy group in compounds of formula II can be protected; for example, by esterification to form a readily cleavable ester such as a silyl ester (e.g. the trimethylsilyl ester) or benzhydryl ester. The carboxy group can also be protected in the form of one of the aforementioned readily hydrolysable esters. Furthermore, the carboxy group can be protected by salt formation with an inorganic or tertiary organic base such as trimethylamine. Possible protecting groups are e.g. benzhydryl, tert. butyl, p-nitrobenzyl, p-methoxy-benzyl or allyl.

The amino group present in the acylating agent of formula III can be protected. Possible protecting groups $R^f$ are, for example, protecting groups which are cleavable by acid hydrolysis (e.g. the tert.butoxycarbonyl or trityl groups) or by basic hydrolysis (e.g. the trifluoroacetyl group). Preferred protecting groups are the phenylacetyl, the chloroacetyl, bromoacetyl and iodoacetyl groups, especially the chloroacetyl group. These last-mentioned protecting groups can be cleaved off by treatment with thiourea. The 7-amino group in compounds II can be protected, for example, by a silyl protecting group such as the trimethylsilyl group.

In reacting a 7-amino compound of formula II with a carboxylic acid of formula III or a reactive functional derivative thereof, for example, a free carboxylic acid can be reacted with an aforementioned ester of a compound of formula II in the presence of a carbodiimide such as dicyclohexylcarbodiimide in an inert solvent such as ethyl acetate, acetonitrile, dioxan, chloroform, methylene chloride, benzene or dimethylformamide, and subsequently the ester group can be cleaved off. Oxazolium salts (e.g. N-ethyl-5-phenyl-isoxazolium-3'-sulphonate) can be used in place of carbodiimides in the foregoing reaction.

According to another embodiment, a salt of an acid of formula II (e.g. a trialkylammonium salt such as the triethylammonium salt) is reacted with a reactive functional derivative of a carboxylic acid of formula III as mentioned earlier in an inert solvent (e.g. one of the aforementioned solvents).

According to a further embodiment, an acid halide, preferably the chloride, of a carboxylic acid of formula III is reacted with an amine of formula II. The reaction is preferably carried out in the presence of an acid-binding agent, for example in the presence of aqueous alkali, preferably sodium hydroxide, or in the presence of an alkali metal carbonate such as potassium carbonate or in the presence of a lower alkylamine such as triethylamine. As the solvent there is preferably used water, optionally in admixture with an inert organic solvent such as tetrahydrofuran or dioxan. The reaction can also be carried out in an aprotic organic solvent such as dimethylformamide, dimethylacetamide, dimethylsulphoxide or hexamethylphosphoric acid triamide. When a silylated compound of formula II is used, the reaction is carried out in an anhydrous medium.

Advantageous alternatives for acylation, where the amino group present in the acylating agent of formula III need not be protected, involves the use of a 2-benzothiazolyl thioester, a 1-hydroxybenzotriazole ester or a mixed anhydride of thiophosphoric acid of the carboxylic acid. For instance, the 2-benzthiazolyl thioester may be reacted with the compound II in an inert organic solvent such as a chlorinated hydrocarbon e.g. methylene chloride, in acetone, ethyl acetate or in a mixture of such solvents with water. The 1-hydroxybenzotriazole ester can be employed by reacting the carboxylic acid with 1-hydroxybenzotriazole and a carbodiimide, especially N,N'-dicyclohexylcarbodiimide or N,N'-diisopropylcarbodiimide in an inert organic solvent, preferably methylene chloride, dimethylformamide, tetrahydrofuran, acetonitrile or ethyl acetate.

The reaction of a 7-amino compound of formula II with the carboxylic acid of formula III or a reactive derivative thereof can conveniently be carried out at a temperature between about −40° C. and +60° C., e.g. at room temperature (about 20° C.).

Embodiment (b) of the process of the present invention involves deprotection (removal) of protected amino, hydroxy or carboxylic groups present in a compound of formula IV and can be carried and as follows:

Removal of amino protecting groups

Possible amino-protecting groups are those employed in peptide chemistry, such as an alkoxycarbonyl group, e.g., t-butoxycarbonyl, etc., a substituted alkoxycarbonyl group, e.g., trichloroethoxycarbonyl etc., an optionally substituted aralkyloxycarbonyl group, e.g., p-nitrobenzyloxycarbonyl or benzyloxycarbonyl, an aralkyl group such as trityl or benzhydryl or a halogen-alkanoyl group such as chloroacetyl, bromoacetyl, iodoacetyl or trifluoroacetyl.

Preferred protecting groups are t-butoxycarbonyl (t-BOC) and trityl.

The amino protecting groups may be cleaved off by acid hydrolysis (e.g. the t-butoxycarbonyl or trityl group), e.g. aqueous formic acid, or by basic hydrolysis (e.g. the trifluoroacetyl group). The chloroacetyl, bromoacetyl and iodoacetyl groups are cleaved off by treatment with thiourea.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). Protecting groups which are cleavable under basic conditions are generally hydrolyzed with dilute aqueous caustic alkali at about 0° C. to 30° C. The chloroacetyl, bromoacetyl and iodoacetyl protecting groups can be cleaved off using thiourea in acidic, neutral or alkaline medium at about 0° C.–30° C.

Removal of hydroxy protecting groups

Possible hydroxy protecting groups are such as are commonly known in the art, e.g.

for protection of hydroxyimino groups ($R^1$=hydrogen in compounds of formula I), usually trityl, lower alkanoyl, preferably acetyl, tetrahydropyranyl protecting groups are employed.

These protecting groups are e.g. removed as follows:

trityl in acidic solvents like 90% formic acid at about 0 to 50° C. or triethylsilane in trifluoroacetic acid at about −20 to 25° C.; in organic solutions of hydrochloric acid at about −50 to 25° C.;

acetyl with weak inorganic bases like sodium bicarbonate in ethanol/water at about 0 to 50° C.; tetrahydropyranyl with weak organic acids like p-toluenesulfonic acid in an alcohol, e.g. ethanol, at about 0° C. to the boiling point of the mixture.

Removal of protecting groups at the carboxy function

As ester protecting groups one may utilize an ester form which can be easily converted into a free carboxyl group under mild conditions, the ester protecting group being exemplified by, for example, t-butyl, p-nitrobenzyl, p-methoxybenzyl, benzhydryl, allyl, etc.

These protecting groups may be removed as follows:

benzhydryl trifluoroacetic acid with anisol, phenol, cresol or triethylsilane at about −40° C. to room temperature; hydrogen with Pd/C in an alcohol such as ethanol or in tetrahydrofuran; $BF_3$-etherate in acetic acid at about 0 to 50° C.;

t-butyl formic acid or trifluoroacetic acid with or without anisol, phenol, cresol or triethylsilane and a solvent such as dichloromethane at about −10° C. to room temperature;

p-nitrobenzyl sodium sulfide in acetone/water at about 0 to room temperature; or hydrogen with Pd/C in an alcohol such as ethanol or in tetrahydrofuran;

p-methoxybenzyl formic acid at about 0 to 50° C.; or trifluoroacetic acid and anisol, phenol or triethylsilane at about −40° C. to room temperature;

allyl palladium(O) catalyzed transalkylation reaction in the presence of sodium or potassium salt of 2-ethyl hexanoic acid, see for example J. Org. Chem. 1982, 47, 587.

In order to make a readily hydrolysable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0–40° C.

Making salts and hydrates of the compounds of formula I or the hydrates of said salts in accordance with embodiment (d) of the process as provided by the present invention can be carried out in a manner known to those of ordinary skill in the art; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt. The temperature at which the salt formation is carried out is not critical. The salt formation is generally carried out at room temperature, but it can be carried out at a temperature slightly above or below room temperature, for example in the range of 0° C. to +50° C.

Making the hydrates usually takes place automatically in the course of the manufacturing process or as a result of the hygroscopic properties of an initially anhydrous product. For the controlled formation of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction schemes 1 and 2 below.

Scheme 1

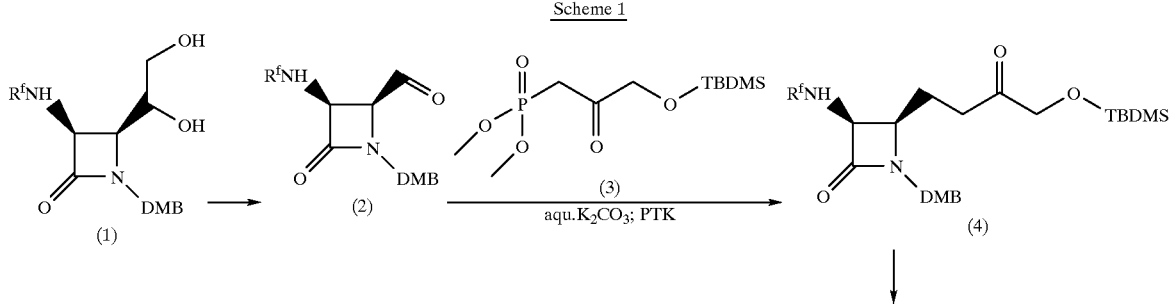

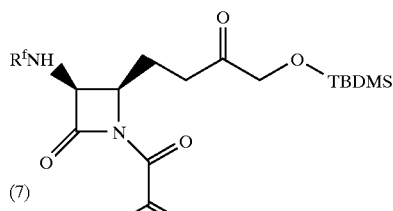
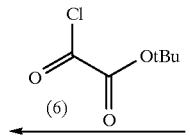
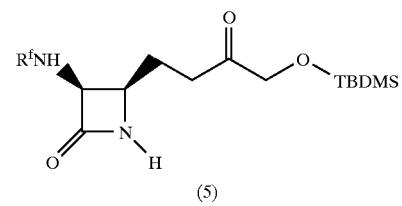

(7)  (6)  (5)

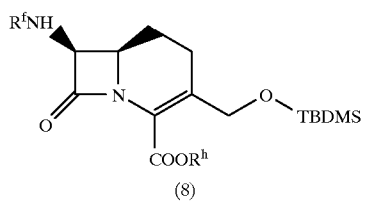
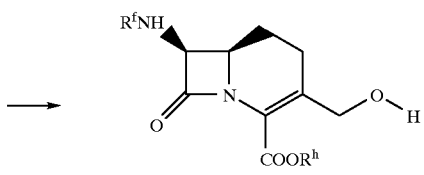

(8)  (9)

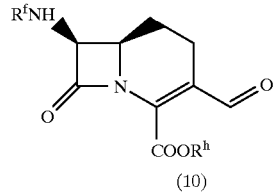

(10)

wherein $R^f$ is an amino protecting group as defined above, $R^h$ is an carboxy protecting group as defined above, PTK stands for phase transfer catalyst, and TBDMS is the tert.butyl-dimethylsilanyloxy group.

(1)→(2)

The 2-(1,2-dihydroxyethyl)-4-oxo-azetidine derivative (1) is oxidized by a standard method to form the aldehyde (2). The oxidation is preferably performed with sodium periodate in an inert solvent as e.g. tetrahydrofuran/water.

(2)→(4)

The aldehyde (2) is reacted with the phosphonic acid ester (3) in the presence of a base, preferably potassium carbonate and of a phase transfer catalyst. The unsaturated addition product is subsequently hydrogenated to form compound (4). The hydrogenation of the double bond is preferably carried out in presence of an catalytic amount of Pd on charcoal in an inert solvent as e.g. ethylacetate.

(4)→(5)

Deprotection of the azetidinone-nitrogen in compound (4) is carried out in a manner known to those of ordinary skill in the art, preferably by addition of potassium persulfate to a solution of (4) in acetonitril, during the reaction the pH of the solution is preferably about 5.

(5)→(7)

After deprotection the azetidinone-nitrogen of (5) is acylated with an appropriate 2-oxo-acetic acid derivative, preferably with 2-chloro-2-oxo-acetic acid tert.butylester (6).

(7)→(8)

Cyclization of compound (7) is preferably carried out in presence of an alkylphosphit and optionally a radical scavenger as for example hydroquinone to form compound (8).

(8)→(9)→(10)

The selective deprotection of the hydroxy group in (8) and the subsequent oxidation of this group to form the aldehyd (10) is carried out according to methods known in the art. Preferred oxidation agents are pyridinium dichromate, manganese dioxide, or sodium hypochlorite in presence of catalytic amounts of piperidin-1-oxyl radicals as TEMPO (2,2,6,6-tetramethylpiperidin-1-oxyl radical) or conditions used for SWERN oxidation.

Scheme 2

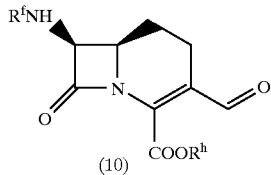
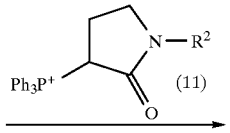
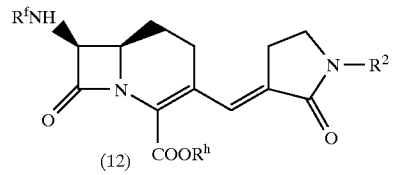

(10)  (11)  (12)

-continued

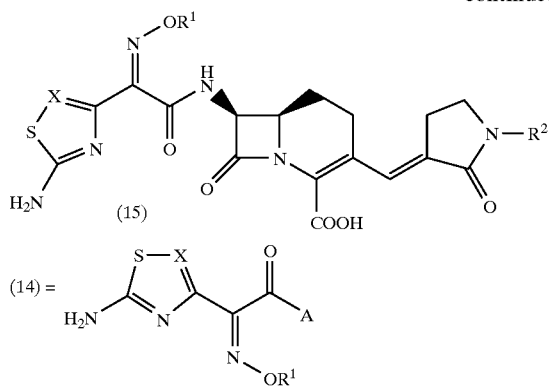

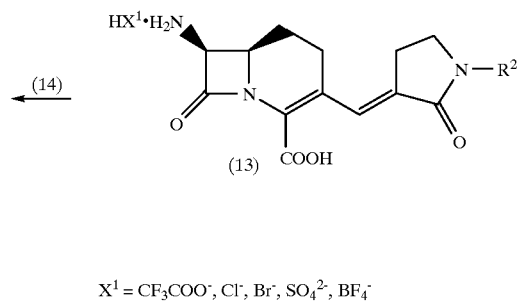

$X^1 = CF_3COO^-, Cl^-, Br^-, SO_4^{2-}, BF_4^-$ (10)→(12)

The reaction of 2-carba-(dethio)-cephem aldehyde (10) where $R^h$ is a carboxy protecting group as defined above, e.g. benzhydryl ester, and $R^f$ is an amino protecting group as defined above, e.g. tert. butyloxycarbonyl, with a Wittig reagent, exemplified by structure (11), yields the coupling product (12). The reaction is carried out in the presence of a base which is either an inorganic base (sodium or potassium hydroxide, sodium or potassium carbonate etc.), an organic base (tertiary amines), an organolithium such as butyl lithium or phenyllithium or an epoxide such as 1,2-butyleneoxide. The reaction in presence of an epoxide is preferred. The preferred solvents, in the case of inorganic base being used, are water and water-miscible solvent (acetone, tetrahydrofuran, or alcohols etc.); in the case of organic base being used, an inert solvent such as methylene chloride, chloroform, benzene, tetrahydrofuran; in the case of organolithium being used, benzene or tetrahydrofuran; and in the case an epoxide being used, the epoxide itself (e.g. 1,2-butyleneoxide). The temperature for the reaction ranges from −20° C. to 110° C. The preferred conditions are exemplified in the examples.

In the normal Wittig reaction according to scheme 2, the E isomer is the predominant product. Invariably, less than 10% Z-isomer is formed, the amount depending on the reagents and conditions.

(12)→(13)

The protecting groups $R^f$ and $R^h$ are removed and the reaction conditions used are depending on the nature of the protecting groups. In the case of $R^f$ being tert-butoxycarbonyl and $R^h$ being benzhydryl, trifluoroacetic acid and anisole or triethylsilane is employed, at temperature of about −20° C. to about room temperature (about 22° C.).

(13)→(15)

The acylation of compound (13) can be carried out with an organic acid (14) which is activated with known reagents A, preferably thionyl chloride, oxalyl chloride, dicyclohexylcarbodiimide, bis-[benzthiazolyl-(2)]disulfide, N-hydroxy-benzotriazole, a 2-halo N-methylpyridinium salt or a mixed anhydride of thiophosphoric acid e.g. of diethylthiophosphoric acid. The reaction is carried out with or without the base (inorganic or organic bases) depending on the method of activation and a wide range of solvents, from water and water-miscible solvent to inert solvents such as chloroform, dimethylformamide (DMF) or dimethylsulfox-ide (DMSO) can be used. The substituents of $R^1$ group, if necessary, can be further deprotected with a reaction condition suitable for the removal of the protecting group.

For the preparation of optionally substituted pyridinium derivatives, i.e. compounds of formula I wherein $R^2$ represent a pyridinium residue the quaternisation of the corresponding pyridine derivative can either be performed subsequent to the Wittig reaction (10)→(12) by substituting compounds (12) wherein $R^2$ is 2-, 3- or 4-pyridinyl in presence of an alkylating agent as for example methyliodide, dimethylsulfate or trimethyloxonium tetrefluoroborate, bromo- or iodoacetamide in a suitable solvent which may be chosen from N,N-dimethylformamide or the like; or the quaternisation can be performed subsequent to the acylation step (13)→(15) under the conditions named above, however, alkylation at this step requires intermediate protection of the other sensitive groups in compound (15). The intermediate protection of these group is preferably carried out with bis(trimethylsilyl)acetamide, see scheme 3.

Scheme 3

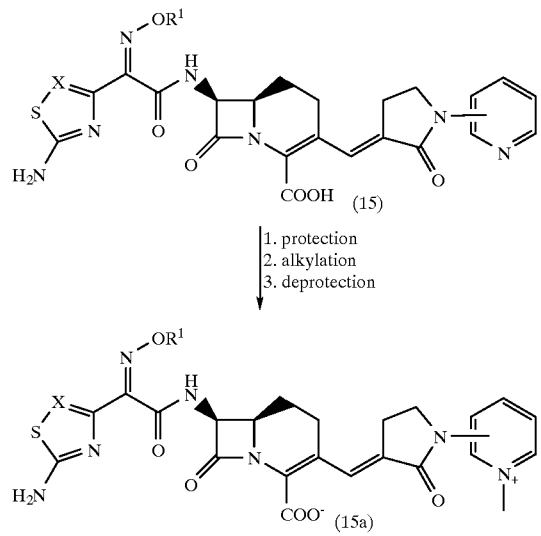

Preferably the quaternisation of the pyridine ring is performed subsequent to the Wittig reaction.

EXAMPLE 1

Synthesis of [(2S, 3S)-1-(2,4-Dimethoxy-benzyl)-2-formyl-4-oxo-azetidin-3-yl]-carbamic acid tert-butyl ester (2)

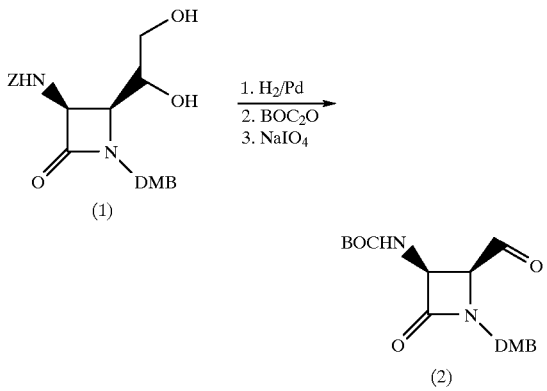

wherein Z is benzyl, DMB is dimethoxybenzyl and BOC is tert.butyloxycarbonyl.

To a solution of 975 g (2.25 Mol) [(2S, 3S)-2-[(R)-1,2-dihydroxy-ethyl]-1-(2,4-dimethoxy-benzyl)-4-oxo-azetidin-3-yl]-carbamic acid benzyl ester (1) in 9.00 l tetrahydrofurane and 1.875 l water was added 112 g palladium 5% on charcoal and the mixture was stirred under a hydrogen atmosphere at 19–22° C. for 2.5 h. The catalyst was removed by filtration and washed with a mixture of 0.75 l tetrahydrofurane and 0.15 l water. To the combined filtrate was added 540 g (2.475 Mol) di-tert-butyl dicarbonate and the mixture was stirred at 23–30° C. for 17 h. A solution of 530 g (2.478 Mol) sodium periodate in 4.05 l water was added at 26–30° C. during 15 min. and stirring was continued for 4 h at 28–30° C. The mixture was diluted with 8.5 l water and 7.5 l ethyl acetate. The phases were separated, the organic phase was washed with 6.75 l of a 10% solution of sodium bicarbonate and with 6.0 l of brine. The aqueous phases were reextracted with 3.7 l of ethyl acetate. The combined organic phases were dried over 2000 g sodium sulfate, filtered and the solids were washed with 2.0 l of ethyl acetate. The combined filtrates were concentrated under aspirator vacuum to yield 940 g of a yellow foam. This foam was dissolved in 1.9 l methylene chloride at 40° C., diluted with 4.5 l n-hexane, concentrated to 4.3 l at 40° C. and 600 mbar and allowed to crystallize for two days. The resulting crystals were collected by filtration, washed with 2.5 l n-hexane and dried under aspirator vacuum at 40° C. for 20 h to yield 816 g [(2S, 3S)-1-(2,4-dimethoxy-benzyl)-2-formyl-4-oxo-azetidin-3-yl]-carbamic acid tert-butyl ester (2) as colorless crystals (97.2% Th.); m.p.: 128–131° C.

$^{1}$H-NMR (CDCl$_3$): 1.40 (s, 9H); 3.76 (s, 3H); 3.80 (s, 3H); 4.12 (d, J=6 Hz, 1H); 4.34 (d, J=14 Hz, 1H); 4.58 (d, J=14 Hz, 1H); 4.87 (dd, J=8 Hz, J=6 Hz, 1H); 5.10 (d, J=8 Hz, 1H) 6.43 (m, 2H); 7.12 (m, 1H); 9.55 (s, 1H) ppm.

EXAMPLE 2

Synthesis of (2R, 3S)-[2-[4-(tert-Butyl-dimethyl-silanyloxy)-3-oxo-butyl]-1-(2,4-dimethoxy-benzyl)-4-oxo-azetidin-3-yl]-carbamic acid tert-butyl ester (4)

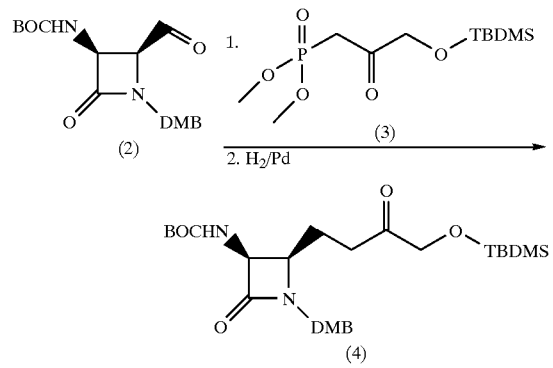

wherein TBDMS is tert.butyl-dimethyl-silanyloxy and the remaining symbols are as defined above.

To a solution of 501 g (1.37 Mol)[(2S, 3S)-1-(2,4-dimethoxy-benzyl)-2-formyl-4-oxo-azetidin-3-yl]-carbamic acid tert-butyl ester (2) in 4.0 l ethyl acetate was added at 0–5° C. 534 g (1.66 Mol) [3-(tert-butyl-dimethyl-silanyloxy)-2-oxo-propyl]-phosphonic acid dimethyl ester (3) and a solution of 303 g (2.2 Mol) potassium carbonate and 47 g (0.14 Mol) tetrabutylammonium hydrogen sulfate in 1.03 l water. This mixture was stirred at 0–5° C. for 3 h. The phases were separated and the organic phase was washed 3 times with 460 ml of a 10% solution of sodium chloride. The aqueous phases were extracted with 400 ml ethyl acetate. The combined organic phases were dried over 600 g sodium sulfate, filtered, the solids were washed with 200 ml ethyl acetate and the combined filtrates were stirred over 50 g palladium 5% on charcoal under a hydrogen atmosphere at normal pressure and room temperature for 5 h. The catalyst was removed by filtration, the solids were washed with 500 ml ethyl acetate. The combined filtrates were concentrated under aspirator vacuum at 40° C. to yield 961 g of a yellow oil. This oil was taken up in ethyl acetate:n-hexane=1:3 and filtered over 2.5 kg of silica gel 60 (230–400 mesh) with ethyl acetate:n-hexane=1:3 as eluent. The fractions pure product containing were combined and concentrated under aspirator vacuum to yield 684 g (2R, 3S)-[2-[4-(tert-butyl-dimethyl-silanyloxy)- 3-oxo-butyl]-1-(2,4-dimethoxy-benzyl)-4-oxo-azetidin-3-yl]-carbamic acid tert-butyl ester (4) as a yellow amorphous solid (90.6% Th.).

$^{1}$H-NMR (DMSO): δ0.01 (s, 6H); 0.84 (s, 9H); 1.38 (s, 9H); 1.56 (m, 1H); 1.75 (m, 1H); 2.23 (m, 2H); 3.42 (m, 1H); 3.74 (s, 3H); 3.77 (s, 3H); 4.05 (d, J=15 Hz, 1H); 4.15 (s, 2H); 4.26 (d, J=15 Hz, 1H); 4.75 (dd, J=10 Hz, J=5 Hz, 1H); 6.46 (dd, J=8 Hz, J=2 Hz, 1H); 6.55 (d, J=2 Hz, 1H); 7.13 (d, J=8 Hz, 1H); 7.78 (d, J=10 Hz, 1H) ppm. MS (ISP): 537.3 (M+H$^+$), 559.3 (M+Na$^+$). IR (KBr): 1455 cm$^{-1}$ (υβ-Lactam CO) MA calc. for C$_{27}$H$_{44}$N$_2$O$_7$Si: C: 60.42; H: 8.26; N: 5.22; found: C: 60.19; H: 8.30; N: 5.16 (%)

EXAMPLE 3

Synthesis of (2R, 3S)-[2-[4-(tert-Butyl-dimethyl-silanyloxy)-3-oxo-butyl]-4-oxo-azetidin-3-yl]-carbamic acid tert-butyl ester (5)

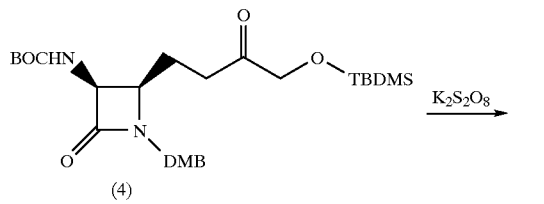

(4)

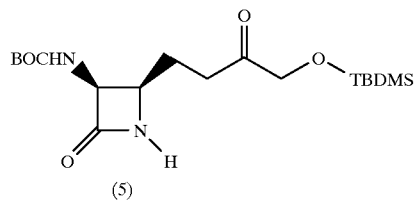

(5)

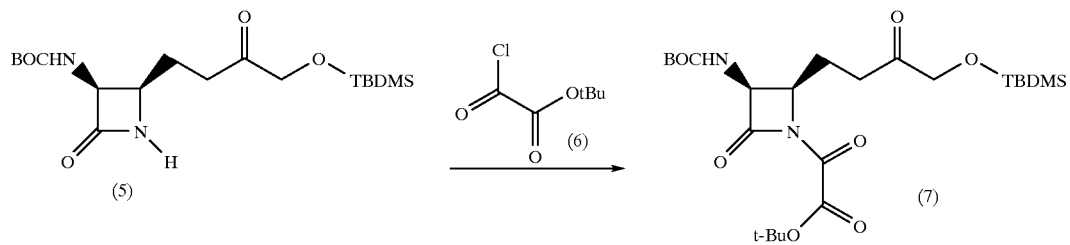

To a solution of 830 g (1.50 Mol) (2R, 3S)-[2-[4-(tert-butyl-dimethyl-silanyloxy)-3-oxo-butyl]-1-(2,4-dimethoxy-benzyl)-4-oxo-azetidin-3-yl]-carbamic acid tert-butyl ester (4) in 8.3 l acetonitrile and 4.15 l water were added in intervals of 25 min three portions of 415 g (1.53 Mol) potassium persulfate at 72–75° C. The pH was kept at 4.9–5.3 by addition of a 10% solution of sodium carbonate (3.75 l). The mixture was stirred at the indicated temperature for 2 h and then cooled to room temperature. The solids were removed by filtration and washed with 5.6 l ethyl acetate. The filtrates were thoroughly mixed. The phases were separated and to the organic layer was added 2.54 l sodium bisulfite 40% in water. The phases were thoroughly mixed, cooled to 5–0° C., stirred for 1 h. The solids were removed by filtration and washed with 0.62 l ethyl acetate. The combined filtrates were stirred and the phases were allowed to separate. The organic phase was consecutively washed with aqueous solutions of 1.86 l sodium chloride (10%), 1.86 l sodium carbonate (5%) and twice with 1.86 l sodium chloride (10%), dried over 1.15 kg sodium sulfate and filtered. The solids were washed with 1.25 l ethyl acetate. To the combined filtrates was added 1.25 kg silica gel 60 (230–400 mesh) and the mixture was concentrated under aspirator vacuum. The remaining solid was charged onto a column containing 3.5 kg silica gel 60 (230–400 mesh). The product was eluted with a gradient of n-hexane:ethyl acetate=2:1 to 1:2. The pure product containing fractions were combined and concentrated under aspirator vacuum and dried 0,1 torr at 45° C. to yield 464 g (2R, 3S)-[2-[4-(tert-butyl dimethyl-silanyloxy)-3-oxo-butyl]-4-oxo-azetidin-3-yl]-carbamic acid tert-butyl ester (5) as a yellow amorphous solid (80% Th.).

$^1$H-NMR (DMSO): 0,04 (s, 6H); 0.87 (s, 9H); 1.39 (s, 9H); 1.58 (m, 2H); 2.36 (m, 2H); 3.48 (m, 1H); 4.24 (s, 2H); 4.73 (dd, J=10 Hz, J=5 Hz, 1H); 7.69 (d, J=10 Hz, 1H); 8.20 (s, 1H) ppm. MS (EI): 313 (M-t-butoxy); 273 [M-(t-butyl)$_2$]. IR (KBr): 1738 cm$^{-1}$ (υβ-Lactam CO) MA calc. for $C_{18}H_{34}N_2O_6Si$): C: 55.93; H: 8.87; N: 7.25; found: C: 55.73; H: 8.91; N: 7.05 (%)

EXAMPLE 4

Synthesis of (2R, 3S)-{3-tert-Butoxycarbonylamino-2-[4-(tert-butyl-dimethyl-silanyloxy)-3-oxo-butyl]-4-oxo-azetidin-1-yl}-oxo-acetic acid tert-butyl ester (7)

wherein t-Bu stands for tert.butyl.

To a solution of 490.7 g (3.0 Mol) chloro-oxo-acetic acid tert-butyl ester (6) in 4.41 l methylene chloride was added 577 g (5.7 Mol) calcium chloride. The suspension was cooled to 0–5° C. A cold (0° C.) solution of 575 g (1.48 Mol) (2R, 3S)-[2-[4-(tert-butyl-dimethyl-silanyloxy)- 3-oxo-butyl]-4-oxo-azetidin-3-yl]-carbamic acid tert-butyl ester (5) and 385 g (3.0 Mol) N,N-diisopropylethylamine was added at such a rate that the temperature does not rise above 5° C. (1.5 h). The reaction mixture was warmed to 23° C. and stirred for 1 h. The solids were removed by filtration and washed with 1.0 l methylene chloride. The combined filtrates were extracted with 1.5 l water, twice with 1.5 l sodium bicarbonate 5% and once again with 1.5 l water. The aqueous phases were extracted with 1.0 l methylene chloride. The combined organic phases were dried over 500 g sodium sulfate and filtered. The solids were washed with 1 l methylene chloride. The combined filtrates were concentrated to a volume of 5.0 l. To this solution 20 l n-hexane was added and the mixture was concentrated to a volume of 10 l. The product was allowed to crystallize while stirring at room temperature for 16 h. The precipitate was collected by filtration, washed with 4 l n-hexane and dried at 0.1 torr at 40° C. to yield 550 g of (2R, 3S)-{3-tert-butoxy carbonylamino-2-[4-(tert-butyl-dimethyl-silanyloxy)-3-oxo-butyl]-4-oxo-azetidin-1-yl}-oxo-acetic acid tert-butyl ester (7) as colorless crystals (69% Th.); m.p.: 102–103° C.

$^1$H-NMR (DMSO): 0,09 (s, 6H); 0.92 (s, 9H); 1.45 (s, 9H); 1.56 (s, 9H); 2.01 (m, 2H); 2.76 (m, 2H); 4.20 (s, 2H); 4.35 (m, 1H); 5.27 (dd, J=9 Hz, J=6 Hz, 1H) ppm. MS (ISP): 532 (M+NH$_4^+$); 537 (M+Na$^+$). IR (KBr): 1811 cm$^{-1}$ (υβ-Lactam CO) MA (calc. for $C_{24}H_{42}N_2O_8Si$): C: 56.01; H: 8.23; N: 5.44; found: C: 55.77; H 8.30; N: 5.43 (%)

EXAMPLE 5

Synthesis of (6R, 7S)-7-tert-Butoxycarbonylamino-3-(tert-butyl-dimethyl-silanyloxymethyl)-8-oxo-1-aza-bicyclo[4.2.0]oct-2-ene-carboxylic acid tert-butyl ester (8)

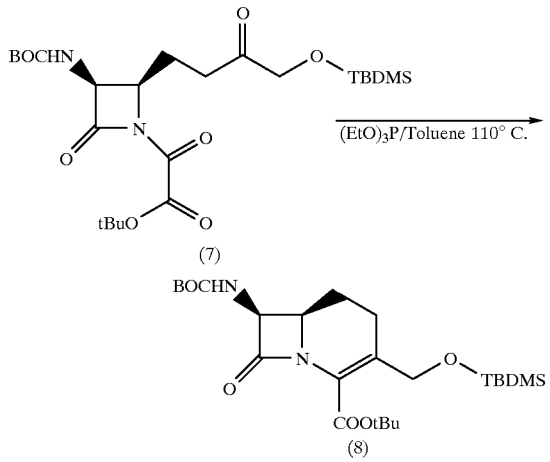

A solution of 560 g (1.09 Mol) (2R, 3S)-(3-tert-butoxycarbonylamino-2-[4-(tert-butyl-dimethyl-silanyloxy)-3-oxo-butyl]-4-oxo-azetidin-1-yl)-oxo-acetic acid tert-butyl ester (7), 890 g (5.35 Mol) triethyl phosphite and 11.1 g (0.10 Mol) hydroquinone in 3.26 l toluene was heated under argon to 70–80° C. for 3 h. The mixture was diluted with 2.3 l toluene and heated to reflux for 24 h. The resulting brown solution was completely evaporated at 60° C., first at aspirator then at high vacuum. The oily residue was taken up in 6.5 l n-hexane and extracted 6 times with 2.0 l of a 2:1 mixture of methanol and water. The aqueous phases were extracted 3 times with 2.0 l n-hexane. The combined hexane phases were dried over 1.1 kg sodium sulfate and filtered. The solids were washed with 2.0 l n-hexane and the combined filtrates were concentrated under aspirator vacuum at 40° C. whereby 415 g (6R, 7S)-7-tert-butoxycarbonylamino-3-(tert-butyl-dimethyl-silanyloxymethyl)-8-oxo-1-aza-bicyclo[4.2.0]oct-2-ene-carboxylic acid tert-butyl ester (8) was obtained as yellowish solid (72% Th.).

$^1$H-NMR (DMSO): 0,06 (s, 3H); 0.07 (s, 3H); 0.89 (s, 9H); 1.45 (s, 9H); 1.58 (s, 9H); 1.58 (m, 1H); 2.1 (m, 1H); 2.45 (m, 2H); 3.8 (m, 1H); 4.40 (d, J=14 Hz, 1H); 4.71 (d, J=14 Hz, 1H); 5.03 (d, J=8 Hz, 1H); 5.14 (dd, J=8 Hz, J=5 Hz, 1H) ppm. MS (ISP): 483.3 (M+H$^+$); 500.4 (M+NH$_4^+$); 505.4 (M+Na$^+$). IR (KBr): 1760 cm$^{-1}$ (υβ-Lactam CO) MA (calc. for C$_{24}$H$_{42}$N$_2$O$_6$Si): C: 59.72; H: 8.77; N: 5.80; found: C: 59.44; H: 8.86; N: 5.68 (%)

EXAMPLE 6

Synthesis of (6R, 7S)-7-tert-Butoxycarbonylamino-3-hydroxymethyl-8-oxo-1-aza-bicyclo[4.2.0]-oct-2-ene-2-carboxylic acid tert-butyl ester (8)

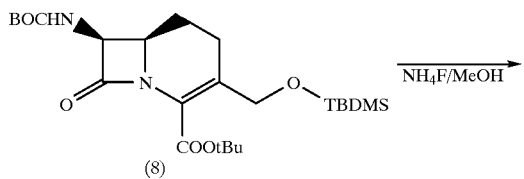

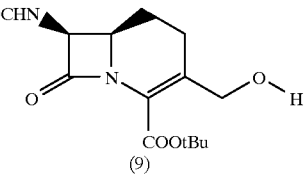

To a solution of 257 g (0.42 Mol) (6R, 7S)-7-tert-butoxycarbonylamino-3-(tert-butyl-dimethyl-silanyloxymethyl)-8-oxo-1-aza-bicyclo[4.2.0]oct-2-ene-carboxylic acid tert-butyl ester (8) in 6.5 l methanol was added 128 g (3.46 Mol) ammonium fluoride. The mixture was stirred at 25° C. for 21 h. The mixture was concentrated to a volume of 0.6 l under aspirator vacuum at 40–45° C. The residue was stirred with 1.2 l water at room temperature for 1 h. The precipitate was collected by filtration, washed twice with 50 ml water, twice with 100 ml of a 1:1 mixture of methanol and water and twice with 50 ml pentane. The solid was dried at 0,1 torr at 30° C. whereby 141.7 g (6R, 7S)-7-tert-butoxycarbonylamino-3-hydroxymethyl-8-oxo-1-aza-bicyclo[4.2.0]-oct-2-ene-2-carboxylic acid tert-butyl ester (9) was obtained as colorless crystals (89% Th.); m.p.: 190–191° C. MS (ISP): 369.3 (M+H$^+$); 391.2 (M+Na$^+$). IR (KBr): 1762 cm$^{-1}$ (υβ-Lactam CO) MA (calc. for C$_{18}$H$_{28}$N$_2$O$_6$): C: 58.68; H: 7.66; N: 7.60; found: C: 58.88; H: 7.69; N: 7.60 (%)

EXAMPLE 7

Synthesis of (6R, 7S)-7-tert-Butoxycarbonylamino-3-formyl-8-oxo-1-aza-bicyclo[4.2.0]oct-2-ene-2-carboxylic acid tert-butyl ester (10)

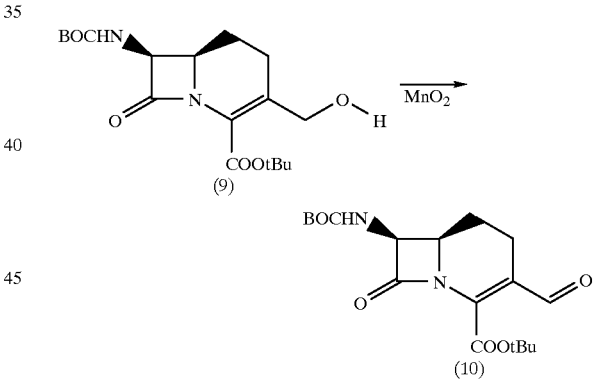

A solution of 194 g (0.52 Mol) of (6R, 7S)-7-tert-butoxycarbonylamino-3-hydroxy-methyl-8-oxo-1-aza-bicyclo[4.2.0]-oct-2-ene-2-carboxylic acid tert-butyl ester (9) in 4.85 l of methylene chloride was stirred with 455 g (0.52 Mol) manganese(IV) oxide at 22–25° C. for 15 h. Another 45.5 g manganese(IV) oxide was added and stirring was continued for 24 h. A further 45.5 g of manganese(IV) oxide was added and stirring was continued for 3.5 h. The solids were removed by filtration over 500 g dicalite and washed with 3 l methylene chloride. The combined filtrates were concentrated under aspirator vacuum and dried at 0.1 torr at 40° C. The residue was dissolved in 182 ml methylene chloride, diluted with 730 ml of pentane and stirred at room temperature for 30 min. The resulting solid was collected by filtration, washed with 140 ml pentane and dried at 0.1 torr at 40° C. to yield 158.5 g (6R, 7S)-7-tert-butoxycarbonylamino-3-formyl-8-oxo-1-aza-bicyclo[4.2.0]

oct-2-ene-2-carboxylic acid tert-butyl ester (10) as colorless crystals (83% Th.); m.p.: 194–195° C.

¹H-NMR (CDCl₃): 1.40 (m, 1H); 1.45 (s, 9H); 1.58 (s, 9H); 2.15 (m, 2H); 2.9 (m, 1H); 3.90 (m, 1H); 5.00 (d, J=8 Hz, 1H); 5.25 (dd, J=8 Hz, J=5 Hz, 1H); 9.94 (s, 1H) ppm. MS (ISP): 367.3 (M+H⁺); 384.3 (M+NH₄⁺); 389.3 (M+Na⁺). IR (KBr): 1786 cm⁻¹ (υβ-Lactam CO) MA (calc. for C₁₈H₂₆N₂O₆): C: 59.00; H: 7.18; N: 7.65; found: C: 58.84; H: 7.17; N: 7.53 (%)

EXAMPLE 8

8.1. Synthesis of (E)-(6R, 7S)-7-tert-Butoxycarbonylamino-8-oxo-3-[2-oxo-1-(2,2,2-trifluoro-ethyl)-pyrrolidin-3-ylidenemethyl]-1-azabicyclo[4.2.0]oct-2-ene-2-carboxylic acid tert-butyl ester

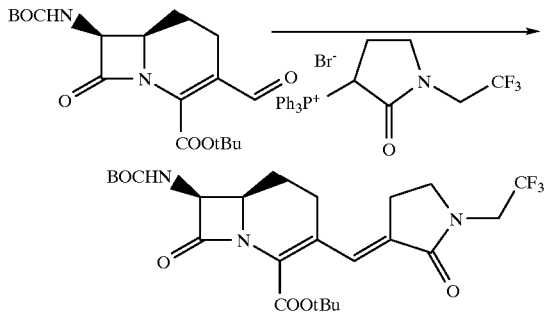

A mixture of 0.50 g (6R, 7S)-7-tert-butoxycarbonylamino-3-formyl-8-oxo-1-aza-bicyclo[4.2.0] oct-2-ene-2-carboxylic acid tert-butyl ester (10) and 0.96 g rac-[2-oxo-1-(2,2,2-trifluoroethyl)-3-pyrrolidinyl]-triphenylphosphonium bromide in 6.0 ml 1,2 epoxybutane was heated to reflux for 6 h. The solvent was evaporated and the residue was purified by chromatography on silica gel using n-hexane:ethyl acetate=3:1 as eluent. The title compound, (E)-(6R, 7S)-7-tert-butoxycarbonylamino-8-oxo-3-[2-oxo-1-(2,2,2-trifluoro-ethyl)-pyrrolidin-3-ylidenemethyl]-1-azabicyclo[4.2.0]oct-2-ene-2-carboxylic acid tert-butyl ester, was obtained as white foam (0.55 g;78% Th).

¹H-NMR (CDCl₃): inter alia 1.45 (s, 9H); 1.57 (s, 9H); 2.00–2.20 (m, 1H); 2.35–2.55 (m, 1H); 2.75–3.10 (m, 3H); 3.50–3.65 (m, 2H); 3.77–3.87 (m, 1H); 3.90–4.10 (m, 2H); 5.05–5.25 (m, 2H); 7.60 (s, 1H) ppm. MS (ISP): 516 (M+H⁺); 533 (M+NH₄⁺); 538 (M+Na⁺). IR (KBr): 1768 cm⁻¹ (υβ-Lactam CO)

In similar manner the following compounds were obtained from (6R, 7S)-7-tert-butoxycarbonylamino-3-formyl-8-oxo-1-aza-bicyclo[4.2.0]oct-2-ene-2-carboxylic acid tert-butyl ester (10) by Wittig reaction with the corresponding phosphonium bromides.

8.2. (E)-(6R, 7S)-tert-Butoxycarbonylamino-3-[1-(4-tert-butoxycarbonyloxy-phenyl)-2-oxo-pyrrolidin-3-ylidenemethyl]-8-oxo-1-aza-bicyclo[4.2.0]oct-2-ene-2-carboxylic acid tert-butyl ester as yellowish crystals, m.p.: 213° C. (dec.)

¹H-NMR (DMSO): inter alia 1.40 (m, 9H); 1.49 (s, 9H); 1.51 (s, 9H);1.6–2.0 (m, 2H); 3.75–3.95 (m, 3H); 5.20 (dd, J=8 Hz, J=5 Hz, 1H); 7.22 (d, J=9 Hz, 2H); 7.45 (s, 1H); 7.76 (d, J=8 Hz, 1H); 7.82 (d, J=9 Hz, 2H) ppm MS (ISP): 626.5 (M+H⁺); 643.5 (M+NH₄⁺). IR (KBr): 1756 cm⁻¹ (υβ-Lactam CO) MA (calc. for C₃₃H₄₃N₃O₉): C: 63.35; H: 6.93; N: 6.72; found: C: 62.92; H: 7.71; N: 6.60

8.3. (E)-(6R, 7S)-tert-Butoxycarbonylamino-3-[1-(3-nitro-phenyl)-2-oxo-pyrrolidin-3-ylidenemethyl]-8-oxo-1-aza-bicyclo[4.2.0]oct-2-ene-2-carboxylic acid tert-butyl ester as yellow solid ¹H-NMR (CDCl₃): inter alia 1.49 (s, 9H); 1.58 (s, 9H); 1.95–2.15 (m, 1H); 2.35–2.55 (m, 1H); 3.00–3.50 (m, 3H); 3.70–4.00 (m, 3H); 3.9–4.05 (m, 1H); 5.24 (dd, J=8 Hz, J=5 Hz, 1H); 6.13 (d, J=8 Hz, 1H); 7.27–7.38 (m, 1H); 7.70–7.80 (m, 1H); 7.85–7.93 (m, 1H); 7.95–8.05 (m, 1H); 8.40 (s, 1H) ppm. MS (ISP): 555.4 (M+H⁺); 572.5 (M+NH₄⁺); 577.4 (M+Na⁺). IR (KBr): 1768 cm⁻¹ (υβ-Lactam CO)

8.4. (E)-(6R, 7S)-7-tert-Butoxycarbonylamino-8-oxo-3-(2-oxo-1-pyridin-2-yl-pyrrolidin-3-ylidenemethyl)-1-azabicyclo[4.2.0]oct-2-ene-2-carboxylic acid tert-butyl ester m.p.: 236° C. (dec.)

¹H-NMR (CDCl₃): 1.46 (m, 9H); 1.58 (s, 9H); 2.37–2.58 (m, 1H); 2.93–3.32 (m, 3H); 3.75–3.85 (m, 1H); 3.90–4.11 (m, 2H); 5.25 (dd, J=8 Hz, J=5 Hz, 1H); 5.89 (d, J=8 Hz, 2H); 6.82–6.92 (m, 1H); 7.50–7.61 (m, 1H); 7.87 (s, 1H); 8.10–8.18 (m, 1H); 8.48 (d, J=8.5 Hz, 1H) ppm. MS (ISP): 511.4 (M+H⁺); 533.4 (M+Na⁺). IR (KBr): 1767 cm⁻¹ (υβ-Lactam CO)

8.5. (E)-(6R, 7S)-7-tert-Butoxycarbonylamino-8-oxo-3-(2-oxo-1-pyridin-3-yl-pyrrolidin-3-ylidenemethyl)-1-azabicyclo[4.2.0]oct-2-ene-2-carboxylic acid tert-butyl ester as beige crystals, m.p.: 243° C. (dec.)

¹H-NMR (CDCl₃): inter alia 1.46 (s, 9H); 1.57 (s, 9H); 2.32–2.52 (m, 1H); 2.96–3.17 (m, 2H); 3.27–3.50 (m, 1H); 3.59–3.95 (m, 3H); 5.24 (dd, J=8 Hz, J=5 Hz, 1H); 6.26 (d, J=8 Hz, 1H); 7.00–7.10 (m, 1H); 7.86 (s, 1H); 8.00–8.10 (m, 1H); 8.17–8.25 (m, 1H); 8.70–8.80 (m, 1H) ppm. MS (ISP): 511.2 (M+H⁺). IR (KBr): 1769 cm⁻¹ (υβ-Lactam CO) MA (calc. for C₂₇H₃₄N₄O₆): C: 63.51; H: 6.71; N: 10.97; found: C: 62.98; H: 6.72; N: 10.97 (%)

8.6. (E)-(6R, 7S)-7-tert-Butoxycarbonylamino-8-oxo-3-(2-oxo-1-pyridin-4-yl-pyrrolidin-3-ylidenemethyl)-1-azabicyclo[4.2.0]oct-2-ene-2-carboxylic acid tert-butyl ester as white crystals, m.p.: 242° C. (dec.)

¹H-NMR (CDCl₃): inter alia 1.46 (s, 9H); 1.58 (s, 9H); 1.95–2.10 (m, 1H); 2.30–2.50 (m, 1H); 2.90–3.15 (m, 2H); 3.20–3.40 (m, 1H); 3.55–3.85 (m, 3H); 5.25 (dd, J=8 Hz, J=5 Hz, 1H); 6.14 (d, J=8 Hz, 1H); 7.48 (d, J=6 Hz, 2H); 7.88 (s, 1H); 8.34 (d, J=6 Hz, 2H) ppm. MS (ISP): 511.5 (M+H⁺). IR (KBr): 1771 cm⁻¹ (υβ-Lactam CO) MA (calc. for C₂₇H₃₄N₄O₆+0.5563 mol C₄H₈O₂): C: 62.06; H: 7.92; N: 9.91 found: C: 61.97; H: 7.79; N: 9.97

8.7. (E)-(6R, 7S)-7-tert-Butoxycarbonylamino-8-oxo-3-(2-oxo-1-piperidin-1-yl-pyrrolidin-3-ylidenemethyl)-1-azabicyclo[4.2.0]oct-2-ene-2-carboxylic acid tert-butyl ester as yellow solid.

MA (calc. for C₂₇H₄₀N₄O₆+0.5563 Mol C₄H₈O₂) C: 62.06; H: 7.92; N: 9.91 found: C: 61.97; H: 7.79; N: 10.08

EXAMPLE 9

(Alkylation of R²=pyridin-2-yl)

9.1. Synthesis of (E)-(6R, 7S)-3-[3-(2-tert-Butoxycarbonyl-7-tert-butoxy-carbonylamino-8-oxo-1-aza-bicyclo[4.2.0] oct-2-en-3-ylmethylene)-2-oxo-pyrrolidin-1-yl]-1-methyl-pyridinium iodide

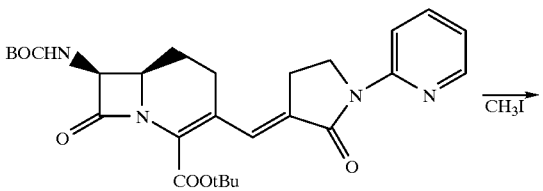

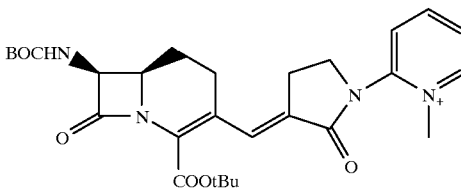

To a solution of 9.50 g (E)-(6R, 7S)-7-tert-butoxycarbonylamino-8-oxo-3-(2-oxo-1-pyridin-3-yl-pyrrolidin-3-ylidenemethyl)-1-aza-bicyclo[4.2.0]oct-2-ene-2-carboxylic acid tert-butylester in 100 ml N,N-dimethylformamide was added 3.17 g methyl iodide and the mixture was stirred at room temperature for 64 h. The solvent was removed by evaporation at 0.1 torr. The residue was triturated in 100 ml ethyl acetate. The yellow solid was collected by filtration. The title compound was obtained as N,N-dimethylformamide solvate (12g, 90% Th). m.p.: 190° C. (dec.)

$^1$H-NMR (CDCl$_3$): inter alia 1.46 (s, 9H); 1.56 (s, 9H); 1.90–2.15 (m, 1H); 2.35–2.55 (m, 1H); 2.90–3.50 (m, 3H); 3.70–3.85 (m, 1H); 3.9–4.05 (m, 1H);4.16–4.35 (m, 1H); 4.69 (s, 3H); 5.28 (dd, J=8 Hz, J=5 Hz, 1H); 6.21 (d, J=8 Hz, 1H); 7.88 (s, 1H); 8.07 (dd, J=15 Hz, J=9 Hz, 1H); 8.79 (d, J=9 Hz, 1H); 9.09 (d, J=15 Hz, 1H); 9.62 (s, 1H) ppm. MS (ISP): 525.5 (M$^+$) IR (KBr): 1765 cm$^{-1}$ (υβ-Lactam CO) MA (calc. for C$_{28}$H$_{37}$N$_4$O$_6$I+0.8 mol C$_3$H$_7$NO): C: 51.35; H: 6.04; N: 9.46; found: C: 51.11; H: 5.83; N: 9.64

In an analogous manner was obtained 9.2. (E)-(6R, 7S)-4-[3-(2-tert-Butoxycarbonyl-7-tert-butoxycarbonylamino-8-oxo-1-aza-bicyclo[4.2.0]oct-2-en-3-ylmethylene)-2-oxo-pyrrolidin-1-yl]-1-methyl-pyridinium iodide.

m.p.: 163° C. (dec.) $^1$H-NMR (DMSO): inter alia 1.40 (s, 9H); 1.52 (s, 9H); 1.50–2.00 (m, 2H); 2.4–2.90 (m, 2H); 3.1–3.40 (m, 2H); 3.80–4.10 (m, 3H); 4.20 (s, 3H); 5.25 (dd, J=8 Hz, J=5 Hz, 1H); 7.57 (s, 1H); 7.75 (d, J=8 Hz, 1H); 8.33 (d, J=7 Hz, 2H); 8.78 (d, J=7 Hz, 1H) ppm. MS (ISP): 525.7 (M$^+$) IR (KBr): 1768 cm$^{-1}$ (υβ-Lactam CO)

9.3. (E)-(6R, 7S)-2-[3-(2-tert-Butoxycarbonyl-7-tert-butoxycarbonylamino-8-oxo-1-aza-bicyclo[4.2.0]oct-2-en-3-ylmethylene)-2-oxo-pyrrolidin-1-yl]-1-methyl-pyridinium tetrafluoroborate.

m.p.: 179° C. (dec.) $^1$H-NMR (DMSO): inter alia 1.41 (s, 9H); 1.49 (s, 9H); 1.50–2.00 (m, 2H); 2.5–3.0 (m, 2H); 3.1–3.50 (m, 2H); 3.80–4.10 (m, 3H); 4.16 (s, 3H); 5.24 (dd, J=8 Hz, J=5 Hz, 1H); 7.51 (s, 1H); 7.77 (d, J=8 Hz, 1H); 8.00–8.10 (m, 1H); 8.16–8.25 (d, J=8 Hz, 1H); 8.63–8.75 (m, 1H); 9.03–9.13 (m, 1H) ppm. MS (ISP): 525.5 (M$^+$) IR (KBr): 1770 cm$^{-1}$ (υβ-Lactam CO)

9.4. (E)-(6R, 7S)-4-[3-(2-tert-Butoxycarbonyl-7-tert-butoxycarbonylamino-8-oxo-1-aza-bicyclo[4.2.0]oct-2-en-3-ylmethylene)-2-oxo-pyrrolidin-1-yl]-1-[(4-tert-butoxycarbonyloxy-3-fluoro-phenylcarbamoyl)-methyl]-pyridinium bromide m.p.: 176° C. $^1$H-NMR (DMSO): inter alia 1.40 (s, 9H); 1.48 (s, 9H); 1.52 (s, 9H); 1.50–2.00 (m, 2H); 2.4–2.90 (m, 2H ); 3.1–3.40 (m, 2H); 3.80–4.10 (m, 3H); 5.25 (dd, J=8 Hz, J=5 Hz, 1H); 5.50 (s, 2H); 7.37 (m, 2H); 7.59 (s, 1H); 7.74 (m, 2H); 8.41 (d, J=7 Hz, 2H); 8.84 (d, J=7 Hz, 1H); 10.94 (s, 1H) ppm. MS (ISP): 778.4 (M$^+$) IR (KBr): 1768 cm$^{-1}$ (υβ-Lactam CO)

EXAMPLE 10

10.1. Synthesis of (E)-(6R, 7S)-7-Amino-8-oxo-3-[2-oxo-1-(2,2,2-trifluoro-ethyl)-pyrrolidin-3-ylidenemethyl]-1-aza-bicyclo[4.2.0]oct-2-ene-2-carboxylic acid

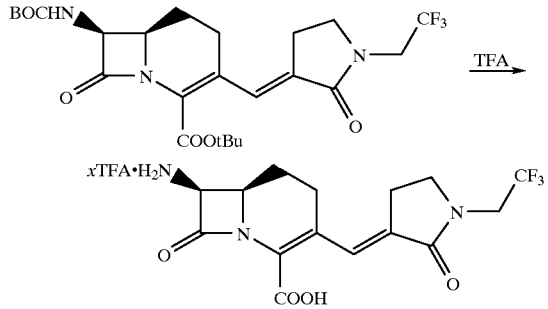

wherein TFA stands for trifluoroacetate and x is the molar fraction as determined by elemental analysis.

A solution of 1.28 g (E)-(6R, 7S)-7-tert-butoxycarbonylamino-8-oxo-3-[2-oxo-1-(2,2,2-trifluoro-ethyl)-pyrrolidin-3-ylidenemethyl]-1-azabicyclo[4.2.0]oct-2-ene-2-carboxylic acid tert-butyl ester in 15 ml trifluoroacetic acid was stirred at room temperature for 2 h. The solvent was removed by evaporation. The residue was triturated with ethyl acetate. The solid was collected by filtration. The title compound was obtained as beige powder. (0.82 g, 86% Th);

m.p.: 237° C. (dec) $^1$H-NMR (DMSO): inter alia 1.54–1.80 (m, 1H); 1.85–2.00 (m, 1H); 2.75–3.25 (m, 3H); 3.4–3.60 (m, 2H); 3.67–3.82 (m, 1H); 4.16 (qu, J=10 Hz, 2H); 4.50 (d, J=5 Hz, 1H); 7.39 (s, 1H)ppm. MS (ISP): 360.4 (M+H$^+$); 377.4 (M+NH$_4^+$); 382.2 (M+Na$^+$). IR (KBr): 1769 cm$^{-1}$ (υβ-Lactam CO) MA (calc. for C$_{15}$H$_{16}$N$_3$O$_4$F$_3$+0.228 mol C$_2$H$_1$O$_2$F$_3$: C: 48.18; H: 4.25; N: 10.90; found: C: 48.13; H: 4.28; N: 10.96

In a similar manner the following 7-amino-carbacephemcarboxylic acids were obtained from their corresponding protected precursors.

10.2. (E)-(6R, 7S)-7-Amino-3-[1-(4-hydroxy-phenyl)-2-oxo-pyrrolidin-3-ylidenemethyl]-8-8-oxo-1-aza-bicyclo[4.2.0]oct-2-ene-2-carboxylic acid as crystallin solid from trifluoroacetic acid m.p.: 151–153° C. (dec) $^1$H-NMR (DMSO): inter alia 1.60–2.00 (m, 2H); 2.80–3.30 (m, 3H); 3.75–4.05 (m, 3H); 4.92 (d, J=5 Hz, 1H); 6.78 (d, J=9 Hz, 2H); 7.47 (s, 1H); 7.56 (d, J=9 Hz, 2H) ppm. MS (ISN): 368.2 (M-H$^+$). IR (KBr): 1769 cm$^{-1}$ (υβ-Lactam CO) MA calc. for C$_{19}$H$_{19}$N$_3$O$_5$+1.8 mol C$_2$H$_1$O$_2$F$_3$: C: 47.25; H: 3.65; N: 7.31; found: C: 47.25; H: 3.80; N: 7.30 (%)

10.3. (E)-(6R, 7S)-7-Amino-3-[1-(3-nitro-phenyl)-2-oxo-pyrrolidin-3-ylidenemethyl]-8-oxo-1-aza-bicyclo[4.2.0]oct-2-ene-2-carboxylic acid as yellow crystals from ethyl acetate, m.p.: 242–243° C. (dec.)

$^1$H-NMR (DMSO): inter alia 1.60–2.15 (m, 2H); 3.80–4.05 (m, 3H); 4.50 (d, J=5 Hz, 1H); 7.55 (s, 1H); 7.65–7.75 (m, 1H); 8.00–8.15 (m. 2H); 8.86 (s br, 1H)ppm. MS (ISN): 397.2 (M—H$^+$). IR (KBr): 1779 cm$^{-1}$ (υβ-Lactam CO) MA (calc. for C$_{19}$H$_{18}$N$_4$O$_6$+0.322 mol C$_2$H$_1$O$_2$F$_3$ and 1.17% water): C: 54.23; H: 4.25; N: 12.88; found: C: 54.14; H: 4.54; N: 12.69 (%)

10.4. (E)-(6R, 7S)-7-Amino-8-oxo-3-(2-oxo-1-piperidin-1-yl-pyrrolidin-3-ylidenemethyl)-1-aza-bicyclo[4.2.0]oct-2-ene-2-carboxylic acid as yellowish solid $^1$H-NMR (DMSO): inter alia 3.60–3.75 (m, 1H); 4.50 (d, J=5 Hz, 1H); 7.25 (s, 1H) ppm. MS (ISP): 361.3 (M+H$^+$); 383.4 (M+Na$^+$). IR (KBr): 1756 cm$^{-1}$ (υβ-Lactam CO)

10.5. (E)-(6R, 7S)-7-Amino-8-oxo-3-(2-oxo-1-pyridin-2-yl-pyrrolidin-3-ylidenemethyl)-1-aza-bicyclo[4.2.0]oct-2-ene-2-carboxylic acid as beige crystals (from water at pH 7.00)

m.p.: 272° C. (dec.) MS (ISN): 353.3 (M-H⁻). IR (KBr): 1763 cm⁻¹ (υβ-Lactam CO) MA (calc. for $C_{18}H_{18}N_4O_4$+ 0.124 mol $C_2H_1O_2F_3$ and 1.37% water): C: 59.48; H: 4.96; N: 15.20; found: C: 59.48; H: 4.90; N: 15.14 (%)

10.6. (E)-(6R, 7S)-7-Amino-8-oxo-3-(2-oxo-1-pyridin-3-yl-pyrrolidin-3-ylidenemethyl)-1-aza-bicyclo[4.2.0]oct-2-ene-2-carboxylic acid trifluoroacetate (1:2) as white crystals ¹H-NMR (DMSO): inter alia 4.92 (d, J=5 Hz, 1H); 7.45–7.55 (m, 2H); 8.25–8.35 (m, 1H); 8.40–8.46 (m, 1H); 9.02–9.10 (m, 1H) ppm. MS (ISP): 355.4 (M+H⁺); 377.3 (M+Na⁺). IR (KBr): 1774 cm⁻¹ (υβ-Lactam CO) MA (calc. for $C_{19}H_{18}N_4O_6$+2 mol $C_2H_1O_2F_3$): C: 45.37; H: 3.46; N: 9.62; found: C: 45.28; H: 3.89; N: 9.60 (%)

10.7. (E)-(6R, 7S)-7-Amino-8-oxo-3-(2-oxo-1-pyridin-4-yl-pyrrolidin-3-ylidenemethyl)-1-aza-bicyclo[4.2.0]oct-2-ene-2-carboxylic acid as white crystals (from water at pH 7.00)

m.p.: 262° C. (dec.) ¹H-NMR (D₂O): inter alia 1.80–2.00 (m, 1H); 2.30–2.45 (m, 1H); 2.6–2.85 (m, 1H); 3.00–3.40 (m, 3H); 4.05–4.25 (m, 3H); 5.00 (d, J=5 Hz, 1H); 7.70 (s, 1H); 8.32 (d, J=7 Hz, 2H); 8.63 (d, J=7 Hz, 2H) ppm. MS (ISP): 355.3 (M+H⁺); 377.3 (M+Na⁺). IR (KBr): 1760 cm⁻¹ (υβ-Lactam CO)

10.8. (E)-(6R, 7S)-7-Amino-3-[1-(1-methyl-pyridin-1-ium-2-yl)-2-oxo-pyrrolidin-3-ylidenemethyl]-8-oxo-1-aza-bicyclo[4.2.0]oct-2-ene-2-carboxylate tetrafluoroborate (1:1) as yellow crystals, m.p.: 183° C. (dec)

¹H-NMR (DMSO): inter alia 4.16 (s, 3H); 4.82 (d, J=5 Hz, 1H); 7.57 (s, 1H); 8.06 (t, J=8 Hz, 1H); 8.21 (d, J=8 Hz, 1H); 8.68 (t, J=8 Hz, 1H); 9.08 (d, J=8 Hz, 1H) ppm. MS (ISP): 369.3 (M+H⁺); 391.4 (M+Na⁺). IR (KBr): 1771 cm⁻¹ (υβ-Lactam CO) MA (calc. for $C_{19}H_{21}N_4O_4BF_4$+0.68 mol $C_2H_1O_2F_3$): C: 45.82; H: 4.10; N: 10.50; found: C: 45.92; H: 4.28; N: 10.21 (%)

10.9. (E)-(6R, 7S)-7-Amino-3-[1-(1-methyl-pyridin-1-ium-3-yl)-2-oxo-pyrrolidin-3-ylidenemethyl]-8-oxo-1-aza-bicyclo[4.2.0]oct-2-ene-2-carboxylate trifluoroacetate (1:1) as yellow crystals, m.p.: >200° C. (dec)

¹H-NMR (DMSO): inter alia 4.40 (s, 3H); 4.81 (d, J=5 Hz, 1H); 7.62 (s, 1H); 8.15 (dd, J=9 Hz, J=6 Hz, 1H); 8.75 (d, J=6 Hz, 1H); 8.87 (d, J=9 Hz, 1H); 9.48 (s, 1H) ppm 10.10. (E)-(6R, 7S)-7-Amino-3-[I-(1-methyl-pyridin-1-ium-4-yl)-2-oxo-pyrrolidin-3-ylidenemethyl]-8-oxo-1-aza-bicyclo[4.2.0]oct-2-ene-2-carboxylatehydroiodide (1:1) as yellow crystals, m.p.: >200° C. (dec)

¹H-NMR (DMSO): inter alia 4.20 (s, 3H); 4.94 (d, J=5 Hz, 1H); 7.66 (s, 1H); 8.32 (d, J=7 Hz, 2H); 8.81 (d, J=7 Hz, 2H) ppm IR (KBr): 1774 cm⁻¹ (υβ-Lactam CO) MS (ISP): 369.4 (M+H⁺); 391.4 (M+Na⁺).

10.11. (E)-(6R, 7S)-7-Amino-3-[1-[1-[(3-fluoro-4-hydroxyphenylcarbamoyl)-methyl]-pyridin-1-ium-4-yl]-2-oxo-pyrrolidin-3-ylidenemethyl]-8-oxo-1-aza-bicyclo[4.2.0]oct-2-ene-2-carboxylate m.p.: 191° C. (dec)

¹H-NMR (DMSO): inter alia 4.00 (m, 3H); 4.92 (d, J=5 Hz, 1H); 5.44 (s, 2H); 6.92 (t, 1H); 7.10 (d, 1H); 7.50 (d, 1H); 7.67 (s, 1H); 8.39 (d, J=7 Hz, 2H); 8.81 (d, J=7 Hz, 2H); 9.76 (s, 1H); 10.60 (s, 1H) ppm IR (KBr): 1771 cm⁻¹ (υβ-Lactam CO) MS (ISP): 522.4 (M+H⁺).

EXAMPLE 11

11.1. Synthesis of (6R, 7S)-7-[(Z)-2-(2-Amino-thiazol-4-yl)-2-cyclopentyloxyimino-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid sodium salt (1:1)

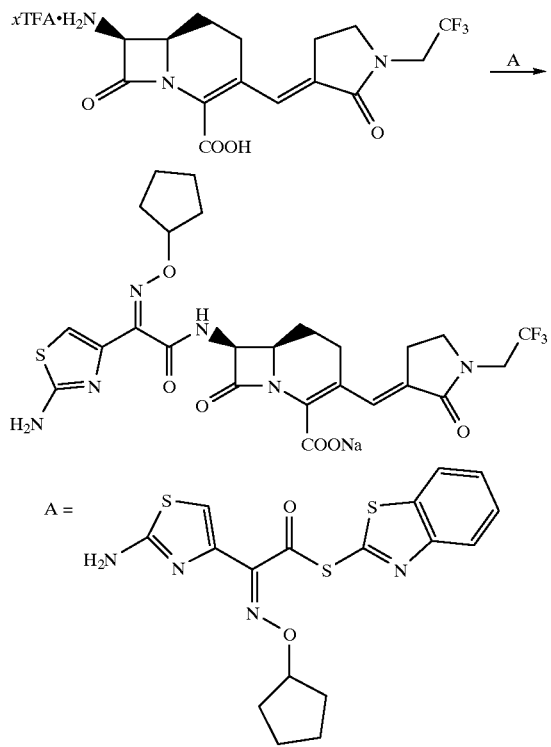

A solution of 0.15 g (E)-(6R, 7S)-7-amino-8-oxo-3-[2-oxo-1-(2,2,2-trifluoro-ethyl)-pyrrolidin-3-ylidenemethyl]-1-aza-bicyclo[4.2.0]oct-2-ene-2-carboxylic acid and 0.25 g (2-amino-thiazol-4-yl)-cyclopentyloxyimino-thioacetic acid S-benzothiazol-2-yl ester in 1.00 ml dimethylformamid was stirred at room temperature for 16 h. The reaction mixture was distributed between water and ethyl acetate at pH 7.00. (1N NaOH was used to adjust the pH) The aqueous phase was purified by chromatography on MCI-gel CHP2OP (75–150 μ) with a continuous gradient of water to 30% acetonitrile in water. The product fractions were combined, concentrated to a volume of ca 25 ml and lyophilized. The title compound was obtained as a slightly beige lyophilisate.

yield 0.21 g (81% Th) ¹H-NMR (DMSO): inter alia 1.40–1.90 (m, 10H); 2.86–3.20 (m, 2H); 3.66–3.80 (m, 1H); 4.00–4.20 (m, 2H); 4.60–4.70 (m, 1H); 5.30 (dd, J=8 Hz, J=5 Hz, 1H); 6.70 (s, 1H); 7.22 (s, 2H); 7.48 (s, 1H); 9.22 (d, J=8 Hz, 1H)ppm. MS (ISP): 597.3 (M—Na⁺+2H⁺). IR (KBr): 1748 cm⁻¹ (υβ-Lactam CO) MA (calc. for $C_{25}H_{26}N_6O_6F_3SNa$+6.88% water: C: 48.54; H: 4.24; N: 13.59; found: C: 48.24; H: 4.21; N: 13.58 (%)

In an analogous manner the following compounds were prepared:

11.2. (6R, 7S)-7-[(Z)-2-(Amino-thiazol-4-yl)-2-cyclopentyloxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid sodium salt (1:1)

¹H-NMR (DMSO): inter alia 1.40–1.95 (m, 10H); 2.90–3.20 (m, 2H); 3.64–3.83 (m, 3H); 4.58–4.72 (m, 1H); 5.30 (dd, J=8 Hz, J=5 Hz, 1H); 6.71 (s, 1H); 6.78 (d, J=9 Hz, 2H); 7.22 (s, 2H); 7.51 (s, 1H); 7.55 (d, J=9 Hz, 2H); 9.24 (d, J=8 Hz, 1H); 9.56 (s, 1H)ppm. MS (ISP): 607.4 (M—Na⁺+2H⁺); 629.4 (M+H⁺). IR (KBr): 1748 cm⁻¹ (υβ-Lactam CO)

11.3. (6R, 7S)-7-[(Z)-2-(2-Amino-thiazol-4-yl)-2-cyclopentyloxyimino-acetylamino]-3-[(E)-1-(3-nitrophenyl)-2-oxo-pyrrolidin-3-ylidenemethyl]-8-oxo-1-aza-bicyclo[4.2.0]oct-2-ene-2-carboxylic acid sodium salt (1:1)

¹H-NMR (DMSO): inter alia 1.40–1.90 (m, 10H); 3.00–3.25 (m, 2H); 3.68–3.98 (m, 3H); 4.60–4.73 (m, 1H); 5.31 (dd, J=8 Hz, J=5 Hz, 1H); 6.71 (s, 1H); 7.22 (s, 2H); 7.60–7.75 (m, 2H); 7.92–8.02 (m, 1H); 8.06–8.17 (m, 1H); 8.77–8.87 (m, 1H); 9.25 (d, J=8 Hz, 1H)ppm. MS (ISP): 636.4 (M—Na⁺+2H⁺); 658.4 (M+H⁺). IR (KBr): 1750 cm⁻¹ (υβ-Lactam CO)

11.4. (6R, 7S)-7-[(Z)-2-(5-Amino-[1,2,4]thiadiazol-3-yl)-2-cyclopentyloximino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid Na salt (1:1)

¹H-NMR (DMSO): inter alia 1.40–1.90 (m, 10H); 2.90–3.25 (m, 2H); 3.65–3.85 (m, 3H); 4.67–4.81 (m, 1H); 5.27 (dd, J=8 Hz, J=5 Hz, 1H); 6.77 (d, J=9 Hz, 2H); 7.51 (s, 1H); 7.54 (d, J=9 Hz, 2H); 8.17 (s, 2H); 9.28 (d, J=8 Hz, 1H); 9.65 (s(br), 1H)ppm. MS (ISP): 608.5 (M—Na⁺+2H⁺); 630.4 (M+H⁺). IR (KBr): 1746 cm⁻¹ (υβ-Lactam CO)

11.5. (6R, 7S)-7-[(Z)-2-(5-Amino-[1,2,4]thiadiazol-3-yl)-2-cyclopentyloxyimino-acetylamino]-3-[(E)-[1-(3-nitro-phenyl)-2-oxo-pyrrolidin-3-ylidenemethyl]-8-oxo-1-aza-bicyclo[4.2.0]oct-2-ene-2-carboxylic acid Na salt (1:1)

¹H-NMR (DMSO): inter alia 1.40–1.90 (m, 10H); 3.00–3.25 (m, 2H); 3.67–3.96 (m, 3H); 4.68–4.78 (m, 1H); 5.28 (dd, J=8 Hz, J=5 Hz, 1H); 7.61–7.83 (m, 2H); 7.92–8.00 (m, 1H); 8.07–8.20 (m, 3H); 8.75–8.85 (m, 1H); 9.28 (d, J=8 Hz, 1H)ppm. MS (ISN): 635.3 (M—Na⁺); 652.3 (M—Na⁺+NH₃) IR (KBr): 1748 cm⁻¹ (υβ-Lactam CO)

11.6. (6R, 7S)-7-[(Z)-2-(2-Amino-thiazol-4-yl)-2-cyclopentyloxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate ¹H-NMR (DMSO): inter alia 1.40–1.90 (m, 10H); 3.70–3.83 (m, 1H); 3.90–4.08 (m, 2H); 4.15 (s, 3H); 4.60–4.71 (m, 1H); 5.32 (dd, J=8 Hz, J=5 Hz, 1H); 6.71 (s, 1H); 7.23 (s, 2H); 7.66 (s, 1H); 7.94–8.04 (m, 1H); 8.13–8.23 (m, 1H); 8.58–8.69 (m, 1H); 9.02–9.10 (m, 1H); 9.27 (d, J=8 Hz, 1H)ppm. MS (ISP): 304.1 (M+2H⁺)/2; 606.4 (M+H⁺). IR (KBr): 1757 cm⁻¹ (υβ-Lactam CO) MA (calc. for C₂₉H₃₁N₇O₆S +9.06% water: C: 57.51; H: 5.16; N: 16.19; found: C: 57.99; H: 4.76; N: 16.30 (%)

11.7. (6R, 7S)-7-[(Z)-2-(2-Amino-thiazol-4-yl)-2-cyclopentyloxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate ¹H-NMR (DMSO): inter alia 1.40–1.90 (m, 10H); 3.65–3.96 (m, 3H); 4.39 (s, 3H); 4.60–4.73 (m, 1H); 5.33 (dd, J=8 Hz, J=5 Hz, 1H); 6.72 (s, 1H); 7.23 (s, 2H); 7.66 (s, 1H); 8.04–8.18 (m, 1H); 8.66–8.75 (m, 1H); 8.86–8.96 (m, 1H); 9.26 (d, J=8 Hz, 1H); 9.40 (s, 1H) ppm. MS (ISP): 304.0 (M+2H⁺)/2; 606.4 (M+H⁺). IR (KBr): 1757 cm⁻¹ (υβ-Lactam CO) MA (calc. for C₂₉H₃₁N₇O₆S +9.06% water: C: 57.51; H: 5.16; N: 16.19; found: C: 57.39; H: 5.20; N: 16.04 (%)

11.8. (6R, 7S)-7-[(Z)-2-(5-Amino-[1,2,4]thiadiazol-3-yl)-cyclopentyloximino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate ¹H-NMR (DMSO): inter alia 1.40–1.90 (m, 10H); 3.66–3.98 (m, 3H); 4.38 (s, 3H); 4.68–4.80 (m, 1H); 5.30 (dd, J=8 Hz, J=5 Hz, 1H); 7.68 (s, 1H); 8.04–8.21 (m, 3H); 8.63–8.72 (m, 1H); 8.80–8.90 (m, 1H); 9.29 (d, J=8 Hz, 1H); 9.40 (s, 1H) ppm. MS (ISP): 607.4 (M+H⁺). IR (KBr): 1756 cm⁻¹ (υβ-Lactam CO)

11.9. (6R, 7S)-7-[(Z)-2-(2-Amino-thiazol-4-yl)-2-cyclopentyloxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate ¹H-NMR (DMSO): inter alia 1.40–1.90 (m, 10H); 3.71–4.00 (m, 3H); 4.17 (s, 3H); 4.60–4.71 (m, 1H); 5.33 (dd, J=8 Hz, J=5 Hz, 1H); 6.71 (s, 1H); 7.23 (s, 2H); 7.70 (s, 1H); 8.27 (d, J=6 Hz, 2H); 8.74 (d, J=6 Hz, 1H); 9.25 (d, J=8 Hz, 1H) ppm. MS (ISP): 606.5 (M+H⁺). IR (KBr): 1756 cm⁻¹ (υβ-Lactam CO)

EXAMPLE 12

Synthesis of (6R, 7S)-7-[(Z)-2-(2-Amino-thiazol-4-yl)-2-hydroxyimino-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid sodium salt (1:1)

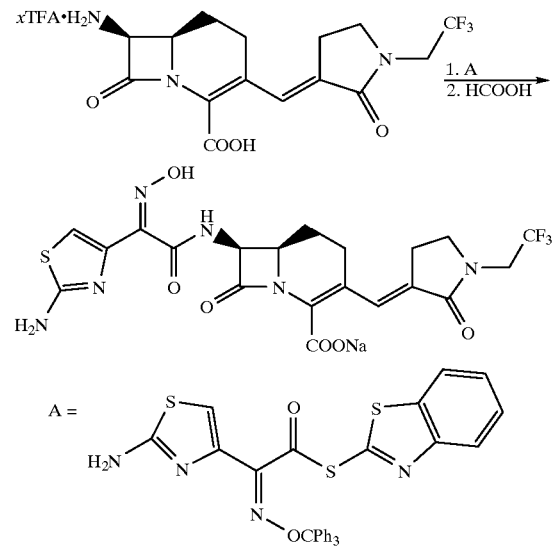

To a solution of 0.15 g (E)-(6R, 7S)-7-amino-8-oxo-3-[2-oxo-1-(2,2,2-trifluoro-ethyl)-pyrrolidin-3-ylidenemethyl]-1-aza-bicyclo[4.2.0]oct-2-ene-2-carboxylic acid in 1.5 ml dimethyl formamide were added 0.40 g (Z)-(2-amino-thiazol-4-yl)-trityloxyimino-acetic acid benzotriazol-1-yl ester and the mixture was stirred at room temperature over night. The solvent was evaporated at 0.1 torr and the residue was taken up in 2 ml formic acid (90%) and stirred at room temperature for 2 h. The precipitate was removed by filtration and the mother liquor was evaporated at 0.1 torr. The residue was purified by chromatography on MCI-gel CHP2OP (75–150 μ) with a continuous gradient of water and acetonitrile. The product containing fractions were combined, concentrated to a volume of ca 25 ml and lyophilized. The title compound was obtained as a slightly beige lyophilisate.

Yield 0.10 g (43% Th)

¹H-NMR (DMSO): inter alia 1.50–2.00 (m, 2H); 3.64–3.78 (m, 1H); 4.00–4.22 (m, 2H); 5.35 (dd, J=8 Hz, J=5 Hz, 1H); 6.67 (s, 1H); 7.13 (s, 2H); 7.50 (s, 1H); 9.16 (d, J=8 Hz, 1H); 11.30 (s, 1H) ppm. MS (ISP): 529.0 (M—Na⁺+2H⁺); 551.1 (M+H⁺). IR (KBr): 1750 cm⁻¹ (υβ-Lactam CO)

In an analogous manner the following compounds were prepared 12.2. (6R, 7S)-7-[(Z)-2-(Amino-thiazol-4-yl)-2-hydroxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid sodium salt (1:1)

¹H-NMR (DMSO): inter alia 1.40–2.00 (m, 2H); 3.60–3.82 (m, 3H); 5.27–5.40 (m, 1H); 6.67–6.83 (m, 3H); 7.12 (s(br), 2H); 7.40–7.60 (m, 4H); 9.48 (s(br)1H); 11.25 (s(br), 1H) ppm. MS (ISP): 539.2 (M—Na⁺+2H⁺); 561.2 (M+H⁻). IR (KBr): 1743 cm⁻¹ (υβ-Lactam CO)

12.3. (6R, 7S)-7-[(Z)-2-(5-Amino-[1,2,4]thiadiazol-3-yl)-2-hydroxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid Na salt (1:1)

¹H-NMR (DMSO): inter alia 1.50–2.00 (m, 2H); 3.60–3.85 (m, 3H); 5.35 (dd, J=8 Hz, J=5 Hz, 1H); 6.79 (d, J=9 Hz, 2H); 7.56 (d, J=9 Hz, 2H); 7.58 (s, 1H); 8.08 (s, 2H); 9.22 (d, J=8 Hz, 1H); 9.84 (s, 1H); 11.96 (s, 1H) ppm. MS (ISP): 540.2 (M—Na⁺+2H⁺); 557.3 (M—Na⁺+NH₃+2H⁺); 562.2 (M+H⁺). IR (KBr): 1745 cm⁻¹ (υβ-Lactam CO)

12.4. (6S, 7R)-7-[(Z)-2-(Amino-thiazol-4-yl)-2-hydroxyimino-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid sodium salt (1:1)

¹H-NMR (DMSO): inter alia 1.50–2.00 (m, 2H); 3.65–4.00 (m, 3H); 5.35 (dd, J=8 Hz, J=5 Hz, 1H); 6.68 (s, 1H); 7.12 (s, 2H); 7.58–7.75 (m, 2H); 7.92–8.00 (m, 1H); 8.04–8.16 (m, 1H); 8.75–8.85 (m, 1H); 9.19 (d, J=8 Hz, 1H); 11.26 (s, 1H) ppm. MS (ISP): 568.3 (M—Na⁺+2H⁺); 590.3 (M+H⁺). IR (KBr): 1748 cm⁻¹ (υβ-Lactam CO)

12.5. (6S, 7R)-7-[(Z)-2-(5-Amino-[1,2,4]thiadiazol-3-yl)-2-hydroxyimino-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid sodium salt (1:1)

¹H-NMR (DMSO): inter alia 1.40–2.00 (m, 2H); 3.65–3.97 (m, 3H); 5.37 (dd, J=8 Hz, J=5 Hz, 1H); 7.60–7.75 (m, 2H); 7.92–8.18 (m, 4H); 9.23 (d, J=8 Hz, 1H); 11.89 (s, 1H) ppm. MS (ISP): 569.3 (M—Na⁺+2H⁺); 586.3 (M—Na⁺+NH₃+2H⁺); 591.3 (M+H⁺). IR (KBr): 1748 cm⁻¹ (υβ-Lactam CO)

12.6. (6R, 7S)-7-[(Z)-2-(2-Amino-thiazol-4-yl)-2-hydroximino-acetylamino]-8-oxo-3-[(E)-2-oxo-1-pyridin-2-yl-pyrrolidin-3-ylidenemethyl]-1-aza-bicyclo[4.2.0]oct-2-ene-2-carboxylic acid Na salt (1:1)

¹H-NMR (DMSO): inter alia 1.50–2.10 (m, 2H); 3.65–4.08 (m, 3H); 5.38 (dd, J=8 Hz, J=5 Hz, 1H); 6.68 (s, 1H); 7.04–7.21 (m, 3H); 7.64 (s, 1H); 7.75–7.88 (m, 1H); 8.31–8.51 (m, 2H); 9.18 (d, J=8 Hz, 1H); 11.30 (s, 1H) ppm. MS (ISP): 524.2 (M—Na⁺+2H⁺); 546.2 (M+H⁺). IR (KBr): 1749 cm⁻¹ (υβ-Lactam CO)

12.7. (6R, 7S)-7-[(Z)-2-(2-Amino-thiazol-4-yl)-2-hydroxyimino-acetylamino]-8-oxo-3-[(E)-2-oxo-1-pyridin-3-yl-pyrrolidin-3-ylidenemethyl]-1-aza-bicyclo[4.2.0]oct-2-ene-2-carboxylic acid Na salt (1:1)

¹H-NMR (DMSO): inter alia 1.50–2.00 (m, 2H); 3.64–3.94 (m, 3H); 5.36 (dd, J=8 Hz, J=5 Hz, 1H); 6.68 (s, 1H); 7.13 (s, 2H); 7.34–7.48 (m, 1H); 7.60 (s, 1H); 8.15–8.35 (m, 2H); 8.92–9.00 (m, 1H); 9.18 (d, J=8 Hz, 1H); 11.25 (s, 1H) ppm. MS (ISP): 524.2 (M—Na⁺+2H⁺); 546.2 (M+H⁺); 568.3 (M+Na⁺). IR (KBr): 1749 cm⁻¹ (υβ-Lactam CO)

12.8. (6R, 7S)-7-[(Z)-2-(2-Amino-thiazol-4-yl)-2-hydroximino-acetylamino]-8-oxo-3-[(E)-2-oxo-1-pyridin-4-yl-pyrrolidin-3-ylidenemethyl]-1-aza-bicyclo[4.2.0]oct-2-ene-2-carboxylic acid Na salt (1:1)

¹H-NMR (DMSO): inter alia 1.50–2.00 (m, 2H); 3.60–3.87 (m, 3H); 5.35 (dd, J=8 Hz, J=5 Hz, 1H); 6.68 (s, 1H); 7.13 (s, 2H); 7.63 (s, 1H); 7.77 (d, J=6 Hz, 2H); 7.99 (d, J=6 Hz, 2H); 9.18 (d, J=8 Hz, 1H); 11.27 (s, 1H) ppm. MS (ISP): 524.2 (M—Na⁺+2H⁺). IR (KBr): 1751 cm⁻¹ (υβ-Lactam CO)

12.9. (6R, 7S)-7-[(Z)-2-(2-Amino-thiazol-4-yl)-2-hydroxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate ¹H-NMR (DMSO): inter alia 1.50–2.00 (m, 2H); 3.68–3.84 (m, 1H); 3.92–4.08 (m.2H); 4.15 (s, 3H); 5.40 (dd, J=8 Hz, J=5 Hz, 1H); 6.68 (s, 1H); 7.13 (s, 2H); 7.66 (s, 1H); 8.00 (t, J=6 Hz, 1H); 8.18 (d, J=6 Hz, 1H); 8.63 (t, J=6 Hz, 1H); 9.04 (d, J=6 Hz, 1H); 9.18 (d, J=8 Hz, 1H); 11.28 (s, 1H) ppm. MS (ISP): 538.4 (M+H⁺). IR (KBr): 1756 cm⁻¹ (υβ-Lactam CO)

12.10. (6R, 7S)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate ¹H-NMR (DMSO): inter alia 1.50–2.00 (m, 2H); 3.64–3.95 (m, 3H); 4.38 (s, 3H); 5.37 (dd, J=8 Hz, J=5 Hz, 1H); 6.68 (s, 1H); 7.14 (s, 2H); 7.69 (s, 1H); 8.04–8.16 (m, 1H); 8.64–8.73 (m, 1H); 8.82–8.91 (m, 1H); 9.19 (d, J=8 Hz, 1H); 9.36–9.47 (m, 1H); 11.27 (s, 1H) ppm. MS (ISP): 538.3 (M+H⁺). IR (KBr): 1752 cm⁻¹ (υβ-Lactam CO)

12.11. (6R, 7S)-7-[(Z)-2-(5-Amino-[1,2,4]thiadiazol-3-yl)-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate ¹H-NMR (DMSO): inter alia 1.40–2.00 (m, 2H); 3.64–3.97 (m, 3H); 4.39 (s, 3H); 5.35 (dd, J=8 Hz, J=5 Hz, 1H); 7.68 (s, 1H); 8.00–8.18 (m, 3H); 8.62–8.73 (m, 1H); 8.80–8.90 (m, 1H); 9.22 (d, J=8 Hz, 1H); 9.35–9.44 (m, 1H); 11.90 (s, 1H) ppm. MS (ISP): 539.2 (M+H⁺). IR (KBr): 1754 cm⁻¹ (υβ-Lactam CO)

12.12. (6R, 7S)-7-[(Z)-2-(2-Amino-thiazol-4-yl)-2-hydroxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate ¹H-NMR (DMSO): inter alia 1.50–2.00 (m, 2H); 3.65–4.00 (m, 3H); 4.17 (s, 3H); 5.40 (dd, J=8 Hz, J=5 Hz, 1H); 6.68 (s, 1H); 7.13 (s, 2H); 7.71 (s, 1H); 8.28 (d, J=6 Hz, 2H); 8.73 (d, J=6 Hz, 2H); 9.19 (d, J=8 Hz, 1H); 11.30 (s, 1H) ppm. MS (ISP): 538.4 (M+H⁺). IR (KBr): 1770 cm⁻¹ (υβ-Lactam CO)

12.13. (6R, 7S)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-4-yl]-2-oxo-pyrrolidin-3-ylidenemethyl]-8-oxo-1-aza-bicyclo[4.2.0]oct-2-ene-2-carboxylate, m.p.: 252° C. (dec)

¹H-NMR (DMSO): inter alia 1.50–2.00 (m, 2H); 3.805–4.00 (m, 3H); 5.50 (m, 3H); 6.71 (s, 1H); 6.92 (t, 1H); 7.16 (s, 1H); 7.25 (d, 2H); 7.62 (d, 1H); 7.96 (s, 1H); 8.35 (d, J=6 Hz, 2H); 8.82 (d, J=6 Hz, 2H); 9.24 (d, J=8 Hz, 1H); 9.74 (s, 1H); 11.31 (s, 1H); 11.72 (s, 1H) ppm. IR (KBr): 1753 cm⁻¹ (υβ-Lactam CO)

EXAMPLE 13

Synthesis of (6R, 7S)-7-[(E)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate By using trifluoroacetic acid and triethyl silane instead of formic acid as described in Example 12 in the deprotection step the (E) oxime isomer is obtained.

¹H-NMR (DMSO): inter alia 1.50–1.90 (m, 2H); 3.60–3.95 (m, 3H); 4.40 (s, 3H); 5.37 (dd, J=8 Hz, J=5 Hz, 1H); 7.20 (s, 2H); 7.53 (s, 1H); 7.66 (s, 1H); 8.03–8.16 (m, 1H); 8.64–8.72 (m, 1H); 8.82–8.91 (m, 1H); 9.16 (d, J=8 Hz, 1H); 9.37–9.43 (m, 1H); 12.57 (s, 1H) ppm.

EXAMPLE 14

14.1. Synthesis of (6R, 7S)-7-[(Z)-2-Acetoxyimino-2-(2-amino-thiazol-4-yl)-acetylamino]-8-oxo-3-[(E)-2-oxo-1-

(2,2,2-trifluoro-ethyl)-pyrrolidin-3-ylidenemethyl]-1-aza-bicyclo[4.2.0]oct-2-ene-2-carboxylic acid sodium salt (1:1)

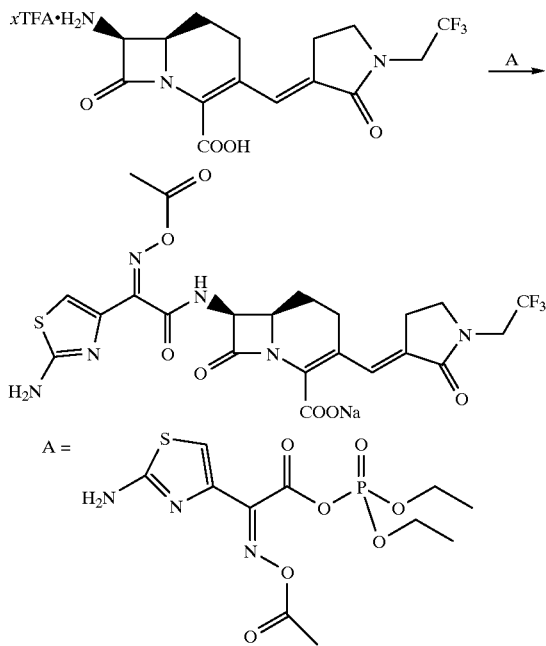

To a solution of 1.90 g (E)-(6R, 7S)-7-amino-8-oxo-3-[2-oxo-1-(2,2,2-trifluoro-ethyl)-pyrrolidin-3-ylidenemethyl]-1-aza-bicyclo[4.2.0]oct-2-ene-2-carboxylic acid and 1,3-bis(trimethylsilyl)urea in 20 ml N,N-dimethylformamide were added 2.42 g (Z)-(2-amino-thiazol-4-yl)-acetoxyimidoacetic acid diethoxy-thiophosphorylester and the mixture was stirred at room temperature for 2 h. The solvent was evaporated at 0.1 torr. The residue was taken up in ethylacetate and the resulting solid was collected by filtration. The raw product was optionally purified by chromatography on MCI-gel CHP2OP (75–150 μ) with a continuous gradient of water and acetonitrile. The product containing fractions were combined, concentrated to a volume of ca 25 ml and lyophilized. The title compound was obtained as a slightly beige lyophilisate.

Yield 1.00 g (after chromatography) $^1$H-NMR (DMSO): inter alia 1.50–1.90 (m, 2H); 2.15 (s, 3H); 3.70–3.85 (m, 1H); 4.00–4.25 (m, 2H); 5.35 (dd, J=8 Hz, J=5 Hz, 1H); 7.09 (s, 1H); 7.37 (s, 2H); 7.50 (s, 1H); 9.56 (d, J=8 Hz, 1H) ppm. MS (ISP): 571.3 (M+H$^+$); 593.3 (M+Na$^+$). IR (KBr): 1756 cm$^{-1}$ (υβ-Lactam CO)

In a similar manner the following compounds were prepared from their corresponding 7-amino-carbacephem precursors 14.2. (6R, 7S)-7-[(Z)-2-Acetoxyimino-2-(2-amino-thiazol-4-yl)-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid $^1$H-NMR (DMSO): inter alia 2.16 (s, 3H); 3.70–4.00 (m, 3H); 5.54 (dd, J=8 Hz, J=5 Hz, 1H); 6.77 (d, J=9 Hz, 2H); 7.11 (s, 1H); 7.37 (s, 2H); 7.44 (s, 1H); 7.55 (d, J=9 Hz, 2H); 9.39 (s, 1H); 9.58 (d, J=8 Hz, 1H)ppm. MS (ISP): 581.3 (M+H$^+$); 603.3 (M+Na$^+$). IR (KBr): 1760 cm$^{-1}$ (υβ-Lactam CO)

14.3. (6R, 7S)-7-[(Z)-2-Acetoxyimino-2-(5-amino-thiazol-3-yl)-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid $^1$H-NMR (DMSO): inter alia 2.17 (s, 3H); 3.80–4.04 (m, 3H); 5.60 (dd, J=8 Hz, J=5 Hz, 1H); 7.12 (s, 1H); 7.37 (s, 2H); 7.56 (s, 1H); 7.68–7.77 (m, 1H); 7.99–8.14 (m, 2H); 8.83–8.92 (m, 1H); 9.60 (d, J=8 Hz, 1H)ppm. MS (ISP): 610.3 (M+H$^+$); 627.3 (M+Na$^+$). IR (KBr): 1765 cm$^{-1}$ (υβ-Lactam CO)

14.4. (6R, 7S)-7-[(Z)-2-Acetoxyimino-2-(2-amino-thiazol-4-yl)-acetylamino]-8-oxo-3-[(Z)-2-oxo-1-pyridin-2-yl-pyrrolidin-3-ylidenemethyl]-1-aza-bicyclo[4.2.0]oct-2-ene-2-carboxylic acid Na salt (1:1)

$^1$H-NMR (DMSO): inter alia 2.16 (s, 3H); 3.75–4.10 (m, 3H); 5.36 (dd, J=8 Hz, J=5 Hz, 1H); 7.06–7.16 (m, 2H); 7.37 (s, 2H); 7.62 (s, 1H); 7.75–7.88 (m, 1H); 8.34–8.50 (m, 2H); 9.58 (d, J=8 Hz, 1H)ppm. MS (ISP): 566.4 (M—Na$^+$+2H$^+$); 588.3 (M+H$^+$). IR (KBr): 1756 cm$^{-1}$ (υβ-Lactam CO)

14.5. (6R, 7S)-7-[(Z)-2-Acetoxyimino-2-(2-amino-thiazol-4-yl)-acetylamino]-8-oxo-3-[(Z)-2-oxo-1-pyridin-3-yl-pyrrolidin-3-ylidenemethyl]-1-aza-bicyclo[4.2.0]oct-2-ene-2-carboxylic acid.

MS (ISP): 566.5 (M+H$^+$). IR (KBr): 1764 cm$^{-1}$ (υβ-Lactam CO)

14.6. (6R, 7S)-7-[(Z)-2-Acetoxyimino-2-(2-amino-thiazol-4-yl)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate $^1$H-NMR (DMSO): inter alia 2.16 (s, 3H); 3.67–3.86 (m, 3H); 4.39 (s, 3H); 5.37 (dd, J=8 Hz, J=5 Hz, 1H); 7.10 (s, 1H); 7.38 (s, 2H); 7.66 (s, 1H); 8.04–8.16 (m, 1H); 8.64–8.73 (m, 1H); 8.85–8.94 (m, 1H); 9.35–9.44 (m, 1H); 9.60 (d, J=8 Hz, 1H)ppm. MS (ISP): 580.3 (M+H$^+$); 602.3 (M+Na$^+$). IR (KBr): 1757 cm$^{-1}$ (υβ-Lactam CO)

14.7. (6R, 7S)-7-[(Z)-2-Acetoxyimino-2-(2-amino-thiazol-4-yl)-acetylamino]-3-[(E)-1-(1-benzyl-piperidin-4-yl)-2-oxo-pyrrolidin-3-ylidenemethyl]-8-oxo-1-aza-bicyclo[4.2.0]oct-2-ene-2-carboxylic acid MS (ISP): 662.4 (M+H)$^+$; 684.3 (M+Na)$^+$. IR (KBr): 1757 cm$^{-1}$ (υβ-Lactam CO)

14.8. (6R, 7S)-7-[(Z)-2-Acetoxyimino-2-(2-amino-thiazol-4-yl)-acetylamino]-8-oxo-3-[(E)-2-oxo-1-piperidin-1-yl-pyrrolidin-3-ylidenemethyl]-1-aza-bicyclo[4.2.0]oct-2-ene-2-carboxylic acid MS (ISP): 572.3 (M+H)$^+$; 594.3 (M+Na)$^+$. IR (KBr): 1765 cm$^{-1}$ (υβ-Lactam CO)

EXAMPLE 15

Synthesis of (6R, 7S)-7-[(Z)-2-Acetoxyimino-2-(2-amino-thiazolo-4-yl)-acetylamino]-3-[(E)-1-(1-carbamoylmethyl-pyridin-1-ium-3-yl)-2-oxo-pyrrolidin-3-ylidenemethyl]-8-oxo-1-aza-bicyclo[4.2.0]oct-2-ene-2-carboxylate

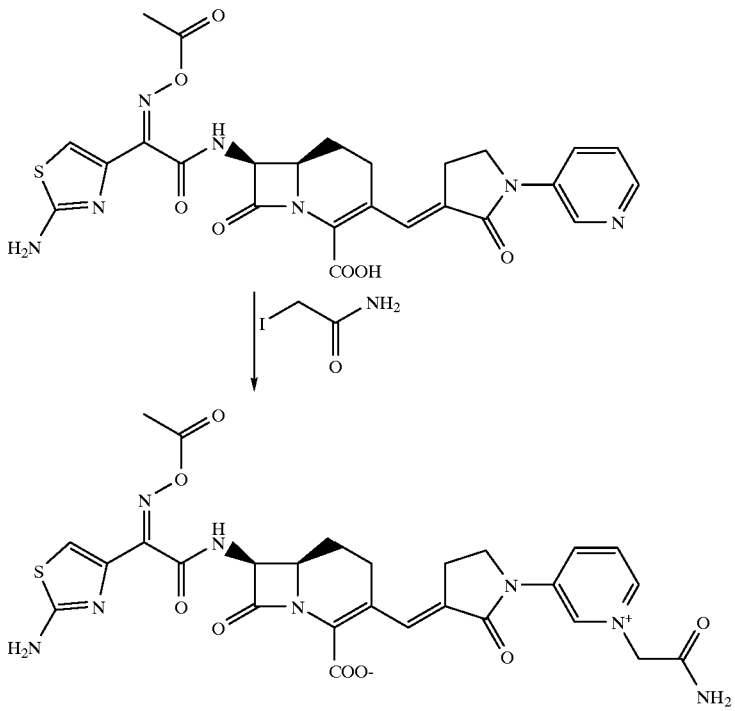

To a solution of 0.17 g (6R, 7S)-7-[(Z)-2-acetoxyimino-2-(2-amino-thiazol-4-yl)-acetylamino]-8-oxo-3-[(Z)-2-oxo-1-pyridin-3-yl-pyrrolidin-3-ylidenemethyl]-1-aza-bicyclo[4.2.0]oct-2-ene-2-carboxylic acid and 0.305 g 1,3-bis(trimethylsilyl)urea in 3 ml N,N-dimethylformamide were added 0.055 g iodoacetamide and the mixture was stirred at room temperature for 72h. The solvent was evaporated at 0.1 torr and the residue was taken up in water. The precipitate was collected by filtration and dried.

Yield: 0.08 g $^1$H-NMR (DMSO): inter alia 2.17 (s, 3H); 3.75–4.05 (m, 3H); 5.46 (s, 2H); 5.52 (dd, J=8 Hz, J=5 Hz, 1H); 7.12 (s, 1H); 7.39 (s, 2H); 7.62 (s, 1H); 7.72 (s, 1H); 8.07 (s, 1H); 8.10–8.26 (m, 1H); 8.67–8.75 (m, 1H); 8.87–8.98 (m, 1H); 9.43–9.54 (m, 1H); 9.60 (d, J=8 Hz, 1H)ppm. MS (ISP): 623.5 (M+H$^+$). IR (KBr): 1761 cm$^{-1}$ (υβ-Lactam CO)

EXAMPLE 16

16.1. Synthesis of (6R, 7S)-7-[(Z)-2-(2-Amino-thiazol-4-yl)-2-methoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate

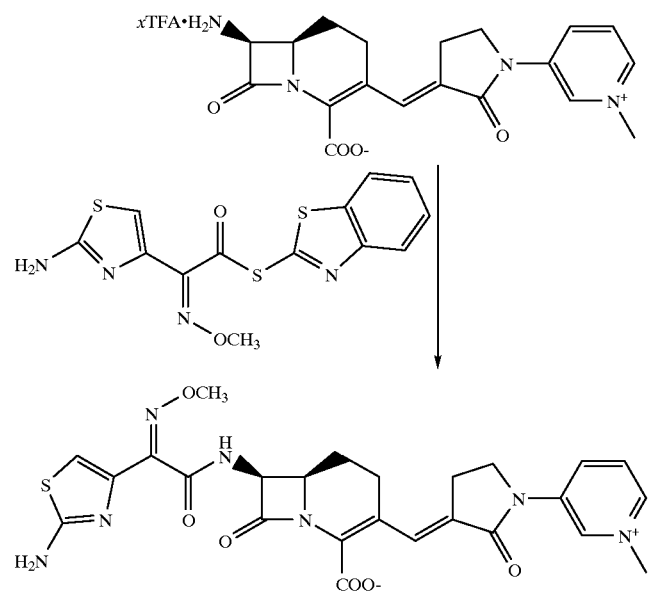

To a suspension of 0.16 g (E)-(6R, 7S)-7-amino-3-[1-(1-methyl-pyridin-1-ium-3-yl)-2-oxo-pyrrolidin-3-ylidenemethyl]-8-oxo-1-aza-bicyclo[4.2.0]oct-2-ene-2-carboxylate trifluoroacetate (1:1) in 1.6 ml N,N-dimethylacetamide were added 0.15 g (Z)-(2-amino-thiazol-4-yl)-methoxyimino-thioacetic acid S-benzothiazol-2-yl ester and the mixture was stirred for 1 h at room temperature. The solvent was evaporated at 0.1 torr and the residue was distributed between water and ethyl acetate. The aqueous phase was purified by chromatography on MCI-gel CHP20P (75–150 μ) with a continuous gradient of water and acetonitrile. The product containing fractions were combined, concentrated to a volume of ca 25 ml and lyophilized. The title compound was obtained as a yellow lyophilisate.

Yield: 0.07 g $^1$H-NMR (DMSO): inter alia 1.40–2.00 (m, 2H); 3.64–3.96 (m, 3H) superimposed by 3.85 (s, 3H); 4.40 (s, 3H); 5.36 (dd, J=8 Hz, J=5 Hz, 1H); 6.76 (s, 1H); 7.23 (s, 2H); 7.65 (s, 1H); 8.04–8.15 (m, 1H); 8.64–8.75 (m, 1H); 8.85–8.96 (m, 1H); 9.32 (d, J=8 Hz, 1H); 9.35–9.45 (m, 1H); ppm. MS (ISP): 552.3 (M+H$^+$); 574.4 (M+Na$^+$). IR (KBr): 1753 cm$^{-1}$ (υβ-Lactam CO)

In a similar manner the following compounds were prepared, using the appropriately substituted (2-Amino-thiazol-4-yl)-oxyimino-thioacetic acid S-benzothiazol-2-yl ester.

16.2. (6R, 7S)-7-[(Z)-2-(2-Amino-thiazol-4-yl)-2-(1-carbamoyl-1-methyl-ethoxyimino)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate $^1$H-NMR (DMSO): inter alia 1.36 (s, 3h); 1.38 (s, 3H); 1.40–2.00 (m, 2H); 3.69–3.97 (m, 3H); 4.39 (s, 3H); 5.36 (dd, J=8 Hz, J=5 Hz, 1H); 6.82 (s, 1H); 6.93 (s, 1H); 7.23 (s, 1H); 7.34 (s, 2H); 7.67 (s, 1H); 8.05–8.15 (m, 1H); 8.65–8.74 (m, 1H); 8.85–8.95 (m, 1H); 9.35–9.44 (m, 1H); 9.48 (d, J=8 Hz, 1H) ppm. MS (ISP): 623.4 (M+H$^+$). IR (KBr): 1757 cm$^{-1}$ (υβ-Lactam CO)

16.3. (6R, 7S)-7-[(Z)-2-(2-Amino-thiazol-4-yl)-2-tert-butoxycarbonylmethoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate $^1$H-NMR (DMSO): inter alia 1.44 (s, 9H); 3.64–3.95 (m, 3H); 4.39 (s, 3H); 4.56 (s, 2H); 5.36 (dd, J=8 Hz, J=5 Hz, 1H); 6.78 (s, 1H); 7.24 (s, 2H); 7.67 (s, 1H); 8.04–8.16 (m, 1H); 8.64–8.74 (m, 1H); 8.81–8.90 (m, 1H); 9.31 (d, J=8 Hz, 1H); 9.37–9.45 (m, 1H); ppm. MS (ISP): 652.4 (M+H$^+$). IR (KBr): 1751 cm$^{-1}$ (υβ-Lactam CO)

EXAMPLE 17

17.1.(6R, 7S)-7-[(Z)-2-(2-Amino-thiazol-4-yl)-2-(1-carboxy-1-methoxyimino)-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate Na salt (1:1).

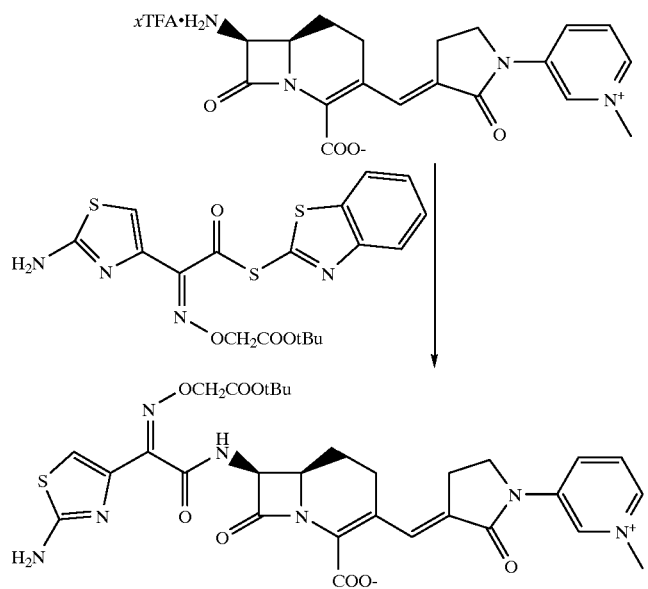

To a suspension of 0.50 g (E)-(6R, 7S)-7-amino-3-[1-(1-methyl-pyridin-1-ium-3-yl)-2-oxo-pyrrolidin-3-ylidenemethyl]-8-oxo-1-aza-bicyclo[4.2.0]oct-2-ene-2-carboxylate trifluoroacetate (1:1) in 2.5 ml N,N-dimethylacetamide were added 0.50 g S-2-benzothiazolyl2-amino-alpha-[(Z)-[1-(tert-butoxycarbonyl)-1-methylethoxy]imino]thio-4-thiazoleacetate and the mixture was stirred for 2.5 h at room temperature. The solvent was evaporated at 0,1 torr and the residue was treated with 5 ml trifluoroacetic acid at room temperature for 1 h. The solvent was evaporated and the residue was distributed between water and ethyl acetate at pH 7.00. The aqueous phase was purified by chromatography on MCI-gel CHP20P (75–150 μ) with a continuous gradient of water and acetonitrile. The product containing fractions were combined, concentrated to a volume of ca 25 ml and lyophilized. The title compound was obtained as a yellow lyophilisate.

Yield: 0.29 g $^1$H-NMR (DMSO): inter alia 1.37 (s, 3H); 1.43 (s, 3H); 3.58–3.88 (m, 3H); 4.41 (s, 3H); 5.50 (dd, J=8 Hz, J=5 Hz, 1H); 6.76 (s, 1H); 7.18 (s, 2H); 7.45 (s, 1H); 8.00–8.11 (m, 1H); 8.99–9.10 (m, 2H); 9.15–9.25 (m, 1H); 11.60 (d(br), J=8 Hz, 1H) ppm. MS (ISP): 624.3 (M—Na$^+$+2H$^+$). IR (KBr): 1752 cm$^{-1}$ (υβ-Lactam CO) MA (calc. for C$_{28}$H$_{28}$N$_7$O$_8$SNa+10.5% water: C: 52.09; H: 4.37; N: 15.19; found: C: 52.05; N: 15.17 (%)

In an analogous manner the following compound was prepared 17.2. (6R, 7S)-7-[(Z)-2-(2-Amino-thiazol-4-yl)-2-(carboxymethoxyimino)-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate Na salt (1:1) was prepared.

$^1$H-NMR (DMSO): inter alia 3.58–3.90 (m, 3H); 4.14–4.31 (m, 2H); 4.41 (s, 3H); 5.45 (dd, J=8 Hz, J=5 Hz, 1H); 6.86 (s, 1H); 7.19 (s, 2H); 7.49 (s, 1H); 8.02–8.12 (m, 1H); 8.81–8.91 (m, 1H); 9.00–9.08 (m, 1H); 9.40–9.49 (m, 1H); 11.46 (d, J=8 Hz, 1H) ppm. MS (ISP): 596.4 (M—Na$^+$+2H$^+$). IR (KBr): 1751 cm$^{-1}$ (υβ-Lactam CO) MA (calc. for C$_{26}$H$_{24}$N$_7$O$_8$SNa+11.29% water: C: 50.57; H: 3.92; N: 15.88; found: C: 50.81; H: 3.90; N: 15.97 (%)

EXAMPLE 18

18.1. Synthesis of (6R, 7S)-7-[(Z)-2-(2-Amino-thiazol-4-yl)-2-(2-fluoro-ethoxyimino)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate

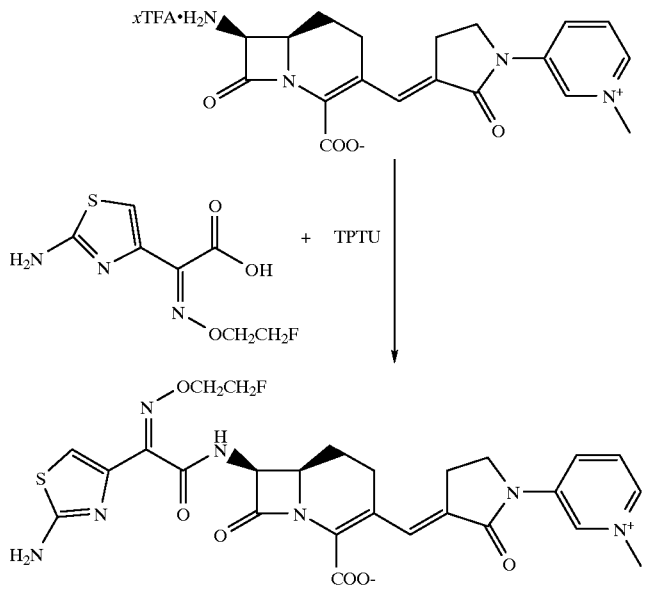

To a solution of 0.23 g (Z)-(2-amino-thiazol-4-yl)-(2-fluoro-ethoxyimino)-acetic acid and 0.15 ml triethylamine in 5.0 ml N,N-dimethylacetamide are added 0.30 g 1,1,3,3-tetramethyl-2-[2-oxo-1(2H)-pyridyl]uronium tetrafluoroborate (1:1) (TPTU) and the mixture was stirred for 10 min at room temperature. To this mixture 0.50 g (E)-(6R, 7S)-7-Amino-3-[1-(1-methyl-pyridin-1-ium-3-yl)-2-oxo-pyrrolidin-3-ylidenemethyl]8-oxo-1-aza-bicyclo[4.2.0]oct-2-ene-2-carboxylate trifluoroacetate (1:1) was added and stirring was continued for 4 h at room temperature. Another 0.30 ml of triethylamine was added and the mixture was stirred for 1 h. The solvent was evaporated and the residue was distributed between water and ethyl acetate at pH 7.00. The aqueous phase was purified by chromatography on MCI-gel CHP2OP (75–150 μ) with a continuous gradient of water and acetonitrile. The product containing fractions were combined, concentrated to a volume of ca 25 ml and lyophilized. The title compound was obtained as a yellow lyophilisate.

Yield: 0.17 g $^1$H-NMR (DMSO): inter alia 1.50–2.00 (m, 2H); 3.64–3.98 (m, 3H); 4.18–4.80 (m, 4H) superimposed by 4.39 (s, 3H); 5.34 (dd, J=8 Hz, J=5 Hz, 1H); 6.79 (s, 1H); 7.25 (s, 2H); 7.66 (s, 1H); 8.03–8.15 (m, 1H); 8.65–8.75 (m, 1H); 8.84–8.94 (m, 1H); 9.36 (d, J=8Hx, 1H) superimposed by 9.36–9.44 (m, 1H) ppm. MS (ISP): 584.4 (M+H$^+$). IR (KBr): 1754 cm$^{-1}$ (υβ-Lactam CO) MA (calc. for C$_{26}$H$_{26}$N$_7$FO$_6$S+7.35% water and 1.3% ashes: C: 53.51; H: 4.49; N: 16.18; found: C: 53.33; H: 4.46; N: 16.38 (%)

We claim:

1. A compound of formula I

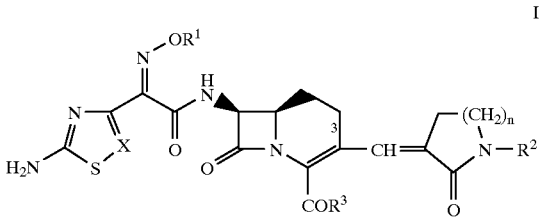

wherein

R$^1$ is hydrogen, lower alkyl which is unsubstituted or substituted by fluoro, aralkyl, cycloalkyl, —COR$^4$, —C(R$^5$R$^6$)CO$_2$R$^7$ or —C(R$^5$R$^6$)CONHR$^7$; where R$^5$ and R$^6$ are each independently hydrogen or lower alkyl, or R$^5$ and R$^6$ taken together with the carbon atom to which these are attached form a cycloalkyl group; R$^4$ is hydrogen or lower alkyl and R$^7$ is hydrogen or a carboxylic acid protecting group;

R$^2$ is hydrogen, hydroxy, lower alkyl-Q$_m$, cycloalkyl, lower alkoxy, lower alkenyl, cycloalkenyl, lower alkynyl, aralkyl-Q$_m$, aryl-Q$_m$, aryloxy, aralkoxy, a heterocyclic ring or heterocyclyl lower alkyl, wherein the heterocyclic ring is an unsaturated or saturated 5-, 6-, or 7-membered heterocyclic ring containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with one group selected from carboxy, amino, nitro, cyano, lower alkyl which is unsubstituted or substituted by fluoro, lower alkoxy, hydroxy, halogen, —COR⁶, —C(R⁵R⁶)CO₂R⁷, —C(R⁵R⁶)CONR⁵R⁸, —CONR⁵R⁶, —N(R⁶)COOR¹⁰, R⁶OCO— or R⁶COO— where R⁵ and R⁶ are hydrogen or lower alkyl; R⁷ is hydrogen or a carboxylic acid protecting group; R⁸ is hydrogen, lower alkyl or phenyl which is unsubstituted or substituted with at least one halogen, hydroxy, amino, lower alkyl or lower alkoxy; R¹⁰ a carboxylic acid protecting group;

Q is —CHR—, —CO— or —SO₂—;

R is hydrogen or lower alkyl;

R³ is hydroxy, —O— when R² is a quaternary heterocyclic ring or a quaternary heterocyclyl lower alkyl, lower alkoxy, —OM and M represents an alkali metal;

m is 0 or 1;

n is 0, 1 or 2;

x is CH or N as well as esters thereof which are readily hydrolyzable in vivo, pharmaceutically acceptable salts of said compounds and hydrates of the compounds of formula I and of their esters and salts.

2. The compound of claim 1, wherein the substituent at position 3 is in the E-form that is, the formula Ia

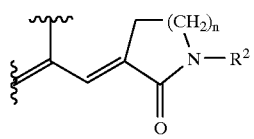

Ia

3. The compound of claim 2, wherein n is 1.

4. The compound of claim 3, wherein X is CH.

5. The compound of claim 4, wherein R is hydrogen, lower alkyl which is unsubstituted or substituted by fluoro, cycloalkyl, —COR⁴, —C(R⁵R⁶)CO₂R⁷, or —C(R⁵R⁶)CONHR⁷.

6. The compound of claim 5, wherein R¹ is hydrogen.

7. The compound of claim 6, wherein R² is lower alkyl-$Q_m$, aryl-$Q_m$, or a heterocycle ring, wherein lower alkyl-$Q_m$, aryl-$Q_m$, and the heterocycle ring are unsubstituted or substituted with at least one group selected from nitro, hydroxy, halogen, lower alkyl, which is unsubstituted or substituted with fluoro, or —C(R⁵R⁶)CONR⁵R⁸.

8. The compound of claim 7, wherein R² is lower alkyl-$Q_m$.

9. The compound of claim 8, wherein m is 0.

10. The compound of claim 9, wherein the lower alkyl is substituted with fluoro.

11. The compound of claim 10, (6R, 7S)-7-[(Z)-2-(2-Amino-thiazol-4-yl)-2-hydroxyimino-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid.

12. The compound of claim 7, wherein R² is aryl-$Q_m$.

13. The compound of claim 12, wherein m is 0.

14. The compound of claim 13, wherein aryl is substituted with at least one group selected from hydroxy or nitro.

15. The compound of claim 14, (6R, 7S)-7-[(Z)-2-(Amino-thiazol-4-yl)-2-hydroxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid.

16. The compound of claim 14, (6S, 7R)-7-[(Z)-2-(Amino-thiazol-4-yl)-2-hydroxyimino-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid.

17. The compound of claim 7, wherein R² is a heterocycle ring.

18. The compound of claim 17, wherein the heterocycle ring is unsubstituted or substituted with at least one group selected from nitro, hydroxy, halogen, lower alkyl which is unsubstituted or substituted with fluoro, or —C(R⁵R⁶)CONR⁵R⁸.

19. The compound of claim 18, wherein the heterocycle ring is unsubstituted.

20. The compound of claim 19, (6R, 7S)-7-[(Z)-2-(2-Amino-thiazol-4-yl)-2-hydroximino-acetylamino]-8-oxo-3-[(E)-2-oxo-1-pyridin-2-yl-pyrrolidin-3-ylidenemethyl]-1-aza-bicyclo[4.2.0]oct-2-ene-2-carboxylic acid.

21. The compound of claim 19, (6R, 7S)-7-[(Z)-2-(2-Amino-thiazol-4-yl)-2-hydroxyimino-acetylamino]-8-oxo-3-[(E)-2-oxo-1-pyridin-3-yl-pyrrolidin-3-ylidenemethyl]-1-aza-bicyclo[4.2.0]oct-2-ene-2-carboxylic acid.

22. The compound of claim 19, (6R, 7S)-7-[(Z)-2-(2-Amino-thiazol-4-yl)-2-hydroximino-acetylamino]-8-oxo-3-[(E)-2-oxo-1-pyridin-4-yl-pyrrolidin-3-ylidenemethyl]-1-aza-bicyclo[4.2.0]oct-2-ene-2-carboxylic acid.

23. The compound of claim 18, wherein the heterocycle ring is substituted with at least one group selected from nitro, hydroxy, halogen, lower alkyl which is unsubstituted or substituted with fluoro, or —C(R⁵R⁶)CONR⁵R⁸.

24. The compound of claim 23, wherein the heterocycle ring is substituted with lower alkyl which is unsubstituted.

25. The compound of claim 24, (6R, 7S)-7-[(Z)-2-(2-Amino-thiazol-4-yl)-2-hydroxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate.

26. The compound of claim 24, (6R, 7S)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

27. The compound of claim 24, (6R, 7S)-7-[(Z)-2-(2-Amino-thiazol-4-yl)-2-hydroxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate.

28. The compound of claim 23, wherein the heterocycle ring is substituted with —C(R⁵R⁶)CONR⁵R⁸.

29. The compound of claim 28, wherein R⁵ is hydrogen and R⁸ is phenyl which is substituted with at least one group selected from hydroxy and halogen.

30. The compound of claim 29, (6R, 7S)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-4-yl]-2-oxo-pyrrolidin-3-ylidenemethyl)-8-oxo-1-aza-bicyclo[4.2.0]oct-2-ene-2-carboxylate.

31. The compound of claim 4, wherein R¹ is lower alkyl which is unsubstituted or substituted by fluoro.

32. The compound of claim 31, wherein R¹ is lower alkyl which is unsubstituted.

33. The compound of claim 32, wherein R² is a heterocycle ring which is substituted with lower alkyl which is unsubstituted.

34. The compound of claim 33, (6R, 7S)-7-[(Z)-2-(2-Amino-thiazol-4-yl)-2-methoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

35. The compound of claim 31, wherein R¹ is lower alkyl which is substituted by fluoro.

36. The compound of claim 35, wherein R¹ is 2-fluoroethyl.

37. The compound of claim 36, wherein $R^2$ is a heterocycle ring which is substituted with lower alkyl which is unsubstituted.

38. The compound of claim 37, (6R, 7S)-7-[(Z)-2-(2-Amino-thiazol-4-yl)-2-(2-fluoro-ethoxyimino)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

39. The compound of claim 4, wherein $R^1$ is —C($R^5R^6$)$CO_2R^7$.

40. The compound of claim 39, wherein $R^5$ and $R^6$ are each hydrogen.

41. The compound of claim 40, wherein $R^2$ is a heterocycle ring which is substituted with lower alkyl which is unsubstituted.

42. The compound of claim 41, wherein $R^7$ is hydrogen.

43. The compound of claim 42, (6R, 7S)-7-[(Z)-2-(2-Amino-thiazol-4-yl)-2-carboxymethoxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

44. The compound of claim 41, wherein $R^7$ is lower alkyl.

45. The compound of claim 44, (6R, 7S)-7-[(Z)-2-(2-Amino-thiazol-4-yl)-2-tert-butoxycarbonylmethoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

46. The compound of claim 39, wherein $R^5$ and $R^6$ are each lower alkyl.

47. The compound of claim 46, wherein $R^5$ and $R^6$ are each methyl.

48. The compound of claim 47, wherein $R^2$ is a heterocycle ring which is substituted with lower alkyl which is unsubstituted.

49. The compound of claim 48, wherein $R^7$ is hydrogen.

50. The compound of claim 49, (6R, 7S)-7-[(Z)-2-(2-Amino-thiazol-4-yl)-2-(1-carboxy-1-methyl-ethoxyimino)-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

51. The compound of claim 4, wherein $R^1$ is —C($R^5R^6$)$CONHR^7$.

52. The compound of claim 51, wherein $R^5$ and $R^6$ are each lower alkyl.

53. The compound of claim 52, wherein $R^5$ and $R^6$ are each methyl.

54. The compound of claim 53, wherein $R^2$ is a heterocycle ring which is substituted with lower alkyl which is unsubstituted.

55. The compound of claim 54, wherein $R^7$ is hydrogen.

56. The compound of claim 55, (6R, 7S)-7-[(Z)-2-(2-Amino-thiazol-4-yl)-2-(1-carbamoyl-1-methyl-ethoxyimino)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

57. The compound of claim 4, wherein $R^1$ is —$COR^4$.

58. The compound of claim 57, wherein $R^4$ is methyl.

59. The compound of claim 58, wherein $R^2$ is lower alkyl-$Q_m$, aryl-$Q_m$, or a heterocycle ring, wherein lower alkyl-$Q_m$, aryl-$Q_m$ and the heterocycle ring are unsubstituted or substituted with at least one group selected from nitro, hydroxy, halogen, lower alkyl which is unsubstituted or substituted with fluoro, or —C($R^5R^6$)$CONR^5R^8$.

60. The compound of claim 59, wherein $R^2$ is lower alkyl-$Q_m$ wherein the lower alkyl is substituted with fluoro.

61. The compound of claim 60, wherein m is 0.

62. The compound of claim 61, (6R, 7S)-7-[(Z)-2-Acetoxyimino-2-(2-amino-thiazol-4-yl)-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid.

63. The compound of claim 59, wherein $R^2$ is aryl-$Q_m$ wherein the aryl is unsubstituted or substituted with at least one group selected from nitro or hydroxy.

64. The compound of claim 63, wherein m is 0.

65. The compound of claim 64, wherein the aryl is substituted with at least one group selected from nitro or hydroxy.

66. The compound of claim 65, (6R, 7S)-7-[(Z)-2-Acetoxyimino-2-(2-amino-thiazol-4-yl)-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid.

67. The compound of claim 65, (6R, 7S)-7-[(Z)-2-Acetoxyimino-2-(2-amino-thiazol-3-yl)-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid.

68. The compound of claim 63, wherein m is 1.

69. The compound of claim 68, wherein the aryl is unsubstituted.

70. The compound of claim 69, (6R, 7S)-7-[(Z)-2-Acetoxyimino-2-(2-amino-thiazol-4-yl)-acetylamino]-3-[(E)-1-(1-benzyl-piperidin-4-yl)-2-oxo-pyrrolidin-3-ylidenemethyl]-8-oxo-1-aza-bicyclo[4.2.0]oct-2-ene-2-carboxylic acid.

71. The compound of claim 59, wherein $R^2$ is a heterocycle ring which is unsubstituted or substituted with lower alkyl which is unsubstituted or —C($R^5R^6$)$CONR^5R^8$.

72. The compound of claim 71, wherein R is a heterocycle ring which is unsubstituted.

73. The compound of claim 72, (6R, 7S)-7-[(Z)-2-Acetoxyimino-2-(2-amino-thiazol-4-yl)-acetylamino]-8-oxo-3-[(E)-2-oxo-1-piperdin-1-yl-pyrrolidin-3-ylidenemethyl]-1-aza-bicyclo[4.2.0]oct-2-ene-2-carboxylic acid.

74. The compound of claim 72, (6R, 7S)-7-[(Z)-2-Acetoxyimino-2-(2-amino-thiazol-4-yl)-acetylamino]-8-oxo-3-[(Z)-2-oxo-1-pyridin-2-yl-pyrrolidin-3-ylidenemethyl]-1-aza-bicyclo[4.2.0]oct-2-ene-2-carboxylic acid.

75. The compound of claim 72, (6R, 7S)-7-[(Z)-2-Acetoxyimino-2-(2-amino-thiazol-4-yl)-acetylamino]-8-oxo-3-[(Z)-2-oxo-1-pyridin-3-yl-pyrrolidin-3-ylidenemethyl]-1-aza-bicyclo[4.2.0]oct-2-ene-2-carboxylic acid.

76. The compound of claim 71, wherein $R^2$ is a heterocycle ring which is substituted with lower alkyl which is unsubstituted or —C($R^5R^6$)$CONR^5R^8$.

77. The compound of claim 76, wherein R2 is a heterocycle ring which is substituted with lower alkyl which is unsubstituted.

78. The compound of claim 77, (6R, 7S)-7-[(Z)-2-Acetoxyimino-2-(2-amino-thiazol-4-yl)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

79. The compound of claim 71, wherein $R^2$ is a heterocycle ring which is substituted with —C($R^5R^6$)—$CONR^5R^8$.

80. The compound of claim 79, wherein each of $R^5$, $R^6$, and $R^8$ are hydrogen.

81. The compound of claim 80, (6R, 7S)-7-[(Z)-2-Acetoxyimino-2-(2-amino-thiazolo-4-yl)-acetylamino]-3-[(E)-1-(1-carbamoylmethyl-pyridin-1-ium-3-yl)-2-oxo-pyrrolidin-3-ylidenemethyl]-8-oxo-1-aza-bicyclo[4.2.0]oct-2-ene-2-carboxylate.

51

82. The compound of claim 4, wherein $R^1$ is cycloalkyl.

83. The compound of claim 82, wherein $R^1$ is cyclopentyl.

84. The compound of claim 83, wherein $R^2$ is lower alkyl-$Q_m$, aryl-$Q_m$, or a heterocycle ring, wherein lower alkyl-$Q_m$, and the heterocycle ring are unsubstituted or substituted with at least one group selected from nitro, hydroxy, halogen, lower alkyl which is unsubstituted or substituted with fluoro, or —C($R^5R^6$)CONR$^5R^8$.

85. The compound of claim 84, R2 is lower alkyl-$Q_m$.

86. The compound of claim 85, wherein m is 0.

87. The compound of claim 86, wherein the lower alkyl is substituted with fluoro.

88. The compound of claim 87, (6R, 7S)-7-[(Z)-2-(2-Amino-thiazol-4yl)-2-cyclopentyloxyimino-acetylamino]-8-oxo-3-[(E)-2-oxo-1-(2,2,2-trifluoro-ethyl)-pyrrolidin-3-ylidenemethyl]-1-aza-bicyclo[4.2.0]oct-2-ene-2-carboxylic acid.

89. The compound of claim 84, wherein R2 is aryl-$Q_m$.

90. The compound of claim 89, wherein m is 0.

91. The compound of claim 90, wherein aryl is substituted with at least one group selected from hydroxy or nitro.

92. The compound of claim 91, (6R, 7S)-7-[(Z)-2-(Amino-thiazol-4-yl)-2-cyclopentyloxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid.

93. The compound of claim 91, (6R, 7S)-7-[(Z)-2-(2-Amino-thiazol-4-yl)-2-cyclopentyloxyimino-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid.

94. The compound of claim 84, wherein $R^2$ is a heterocycle ring.

95. The compound of claim 94, wherein the heterocycle ring is substituted with lower alkyl which is unsubstituted.

96. The compound of claim 94, (6R, 7S)-7-[(Z)-2-(2-Amino-thiazol-4-yl)-2-cyclopentyloxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate.

97. The compound of claim 94, (6R, 7S)-7-[(Z)-2-(2-Amino-thiazol-4-yl)-2-cyclopentyloxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

98. The compound of claim 94, (6R, 7S)-7-[(Z)-2-(2-Amino-thiazol-4-yl)-2-cyclopentyloxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate.

99. The compound of claim 3, wherein X is N.

100. The compound of claim 99, wherein $R^1$ is hydrogen or cycloalkyl.

101. The compound of claim 100, wherein $R^1$ is hydrogen.

102. The compound of claim 101, wherein $R^2$ is aryl-$Q_m$ or a heterocycle ring, wherein aryl-$Q_m$ and the heterocycle ring are unsubstituted or substituted with at least one group selected from nitro, hydroxy, halogen, lower alkyl which is unsubstituted or substituted with fluoro, or —C($R^5R^6$)CONR$^5R^8$.

103. The compound of claim 102, wherein $R^2$ is aryl-$Q_m$.

104. The compound of claim 103, wherein m is 0.

105. The compound of claim 104, wherein aryl is substituted with at least one group selected from hydroxy or nitro.

106. The compound of claim 105, (6S, 7R)-7-[(Z)-2-(5-Amino-[1,2,4]-thiadiazol-3-yl)-2-hydroxyimino-acetylamino]-3-[(E)-1-(3-nitro-phenyl)-2-oxo-pyrrolidin-3-ylidenemethyl]-8-oxo-1-aza-bicyclo[4.2.0]oct-2-ene-2-carboxylic acid.

107. The compound of claim 105, (6R, 7S)-7-[(Z)-2-(5-Amino-[1,2,4]thiadiazol-3-yl)-2-hydroxyimino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid.

108. The compound of claim 102, wherein $R^2$ is a heterocycle ring.

109. The compound of claim 108, wherein the heterocycle ring is substituted with lower alkyl which is unsubstituted.

110. The compound of claim 109, (6R, 7S)-7-[(Z)-2-(5-Amino-[1,2,4]-thiadiazol-3-yl)-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

111. The compound of claim 100, wherein $R^1$ is hydrogen.

112. The compound of claim 111, wherein $R^2$ is aryl-$Q_m$ or a heterocycle ring, wherein aryl-$Q_m$ and the heterocycle ring are unsubstituted or substituted with at least one group selected from nitro, hydroxy, halogen, lower alkyl which is unsubstituted or substituted with fluoro, or —C($R^5R^6$)CONR$^5R^8$.

113. The compound of claim 112, wherein $R^2$ is aryl-$Q_m$.

114. The compound of claim 113, wherein m is 0.

115. The compound of claim 114, wherein aryl is substituted with at least one group selected from hydroxy or nitro.

116. The compound of claim 115, (6R, 7S)-7-[(Z)-2-(5-Amino-[1,2,4]thiadiazol-3-yl)-2-cyclopentyloximino-acetylamino]-3-[(E)-1-(4-hydroxy-phenyl)-2-oxo-pyrrolidin-3-ylidenemethyl]-8-oxo-1-aza-bicyclo[4.2.0]oct-2-ene-2-carboxylic acid.

117. The compound of claim 115, (6R, 7S)-7-[(Z)-2-(5-Amino-[1,2,4]thiadiazol-3-yl)-2-cyclopentyloxyimino-acetylamino]-3-[(E)-[1-(3-nitro-phenyl)-2-oxo-pyrrolidin-3-ylidenemethyl]-8-oxo-1-aza-bicyclo[4.2.0]oct-2-ene-2-carboxylic acid.

118. The compound of claim 112, wherein $R^2$ is a heterocycle ring.

119. The compound of claim 118, wherein the heterocycle ring is substituted with lower alkyl which is unsubstituted.

120. The compound of claim 119, (6R, 7S)-7-[(Z)-2-(5-Amino-[1,2,4]thiadiazol-3-yl)-cyclopentyloximino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

121. A compound of formula II wherein $R^2$ is hydrogen, hydroxy, lower alkyl-$Q_m$, cycloalkyl, lower alkoxy, lower alkenyl, cycloalkenyl, lower alkynyl, aralkyl-$Q_m$, aryl-$Q_m$, aryloxy, aralkoxy, a heterocyclic ring or heterocyclyl lower alkyl, wherein the heterocyclic ring is an unsaturated or saturated 5-, 6-, or 7-membered heterocyclic ring containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, cyano, lower alkyl which is unsubstituted or substituted by fluoro, lower alkoxy, hydroxy, halogen, —$COR^6$, —$C(R^5R^6)CO_2R^7$, —$C(R^5R^6)CONR^5R^8$, —$CONR^5R^6$, —$N(R^6)COOR^{10}$, $R^6OCO$— or $R^6COO$— where $R^5$ and $R^6$ are hydrogen or lower alkyl; $R^7$ is hydrogen or a carboxylic acid protecting group; $R^8$ is hydrogen, lower alkyl or phenyl which is unsubstituted or substituted with at least one halogen, hydroxy, amino, lower alkyl or lower alkoxy; $R^{10}$ is a carboxylic acid protecting group;

Q is —CHR—, —CO— or —$SO_2$—;

R is hydrogen or lower alkyl;

m is 0 or 1; and n is 0 or 1;

or esters or salts thereof.

122. A pharmaceutical composition comprising a therapeutically effective amount of a compound of formula I

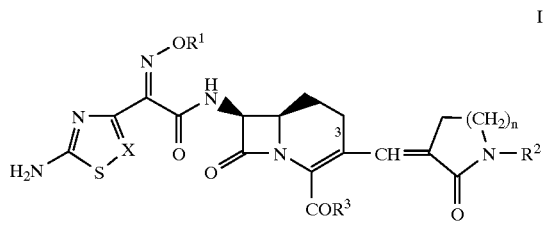

wherein $R^1$ is hydrogen, lower alkyl which is unsubstituted or substituted by fluoro, aralkyl, cycloalkyl, —$COR^4$, —$C(R^5R^6)CO_2R^7$ or —$C(R^5R^6)CONHR^7$; where $R^5$ and $R^6$ are each independently hydrogen or lower alkyl, or $R^5$ and $R^6$ taken together form a cycloalkyl group; $R^4$ is hydrogen or lower alkyl and $R^7$ is hydrogen or a carboxylic acid protecting group;

$R^2$ is hydrogen, hydroxy, lower alkyl-$Q_m$, cycloalkyl, lower alkoxy, lower alkenyl, cycloalkenyl, lower alkynyl, aralkyl-$Q_m$, aryl-$Q_m$, aryloxy, aralkoxy, a heterocyclic ring or heterocyclyl lower alkyl, wherein the heterocyclic ring is an unsaturated or saturated 5-, 6-, or 7-membered heterocyclic ring containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with one group selected from carboxy, amino, nitro, cyano, lower alkyl which is unsubstituted or substituted by fluoro, lower alkoxy, hydroxy, halogen, —$COR^6$, —$C(R^5R^6)CO_2R^7$, —$C(R^5R^6)CONR^5R^8$, —$CONR^5R^6$, —$N(R^6)COOR^{10}$, $R^6OCO$— or $R^6COO$— where $R^5$ and $R^6$ are hydrogen or lower alkyl; $R^7$ is hydrogen or a carboxylic acid protecting group; $R^8$ is hydrogen, lower alkyl or phenyl which is unsubstituted or substituted with at least one halogen, hydroxy, amino, lower alkyl or lower alkoxy; $R^{10}$ is a carboxylic acid protecting group;

Q is —CHR—, —CO— or —$SO_2$—;

R is hydrogen or lower alkyl;

$R^3$ is hydroxy, —O— when $R^2$ is a quaternary heterocyclic ring or a quaternary heterocyclyl lower alkyl, lower alkoxy, —OM and M represents an alkali metal;

m is 0 or 1;

n is 0, 1 or 2;

x is CH or N as well as esters thereof which are readily hydrolyzable in vivo, pharmaceutically acceptable salts of said compounds and hydrates of the compounds of formula I and of their esters and salts, and a pharmaceutically acceptable carrier.

123. The composition of claim 122, wherein X is CH.

124. The composition of claim 123, wherein $R^2$ is a heterocycle ring which is substituted by lower alkyl which is unsubstituted or —$C(R^5R^6)CONR^5R^6$.

125. The composition of claim 124, wherein $R^2$ is a heterocycle ring which is substituted by lower alkyl which is unsubstituted.

126. The composition of claim 125, wherein $R^1$ is hydrogen.

127. The composition of claim 126, (6R, 7S)-7-[(Z)-2-(2-Amino-thiazol-4-yl)-2-hydroxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate.

128. The composition of claim 126, (6R, 7S)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

129. The composition of claim 126, (6R, 7S)-7-[(Z)-2-(2-Amino-thiazol-4-yl)-2-hydroxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate.

130. The composition of claim 125, wherein $R^1$ is lower alkyl which is unsubstituted.

131. The composition of claim 130, (6R, 7S)-7-[(Z)-2-(2-Amino-thiazol-4-yl)-2-methoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

132. The composition of claim 125, wherein $R^1$ is cycloalkyl.

133. The composition of claim 132, wherein $R^1$ is cyclopentyl.

134. The composition of claim 133, (6R, 7S)-7-[(Z)-2-(2-Amino-thiazol-4-yl)-2-cyclopentyloxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate.

135. The composition of claim 133, (6R, 7S)-7-[(Z)-2-(2-Amino-thiazol-4-yl)-2-cyclopentyloxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

136. The composition of claim 125, wherein $R^1$ is —$COR^4$.

137. The composition of claim 136, wherein $R^4$ is hydrogen.

138. The composition of claim 137, (6R, 7S)-7-[(Z)-2-Acetoxyimino-2-(2-amino-thiazol-4-yl)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

139. The composition of claim 124, wherein $R^2$ is a heterocycle ring which is substituted by —$C(R^5R^6)CONR^5R^6$.

140. The composition of claim 139, wherein each of $R^5$, $R^6$, and $R^8$ are hydrogen.

141. The composition of claim 140, (6R, 7S)-7-[(Z)-2-Acetoxyimino-2-(2-amino-thiazolo-4-yl)-acetylamino]-3-[(E)-1-(1-carbamoylmethyl-pyridin-1-ium-3-yl)-2-oxo-pyrrolidin-3-ylidenemethyl]-8-oxo-1-aza-bicyclo[4.2.0]oct-2-ene-2-carboxylate.

142. The composition of claim 122, wherein X is N.

143. The composition of claim 142, wherein $R^2$ is a heterocycle ring which is substituted by lower alkyl which is unsubstituted or —C(R$^5$R$^6$)CONR$^5$R$^6$.

144. The composition of claim 143, wherein $R^2$ is a heterocycle ring which is substituted by lower alkyl which is unsubstituted.

145. The composition of claim 144, wherein $R^1$ is hydrogen.

146. The composition of claim 144, (6R, 7S)-7-[(Z)-2-(5-Amino-[1,2,4]thiadiazol-3-yl)-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

147. The composition of claim 144, wherein $R^1$ is cycloalkyl.

148. The composition of claim 147, wherein $R^1$ is cyclopentyl.

149. The composition of claim 148, (6R, 7S)-7-[(Z)-2-(5-Amino-[1,2,4]thiadiazol-3-yl)-cyclopentyloxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

150. A method for treating bacterial infections in a mammal comprising administering to said mammal a compound of formula I

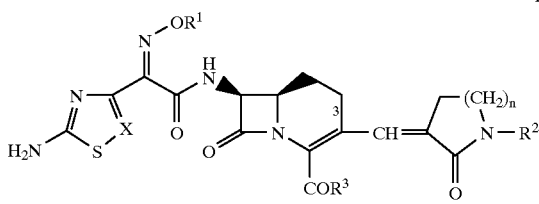

wherein
$R^1$ is hydrogen, lower alkyl which is unsubstituted or substituted by fluoro, aralkyl, cycloalkyl, —COR$^4$, —C(R$^5$R$^6$)CO$_2$R$^7$ or —C(R$^5$R$^6$)CONHR$^7$; where $R^5$ and $R^6$ are each independently hydrogen or lower alkyl, or $R^5$ and $R^6$ taken together form a cycloalkyl group; $R^4$ is hydrogen or lower alkyl and $R^7$ is hydrogen or a carboxylic acid protecting group;

$R^2$ is hydrogen, hydroxy, lower alkyl-Q$_m$, cycloalkyl, lower alkoxy, lower alkenyl, cycloalkenyl, lower alkynyl, aralkyl-Q$_m$, aryl-Q$_m$, aryloxy, aralkoxy, a heterocyclic ring or heterocyclyl lower alkyl, wherein the heterocyclic ring is an unsaturated or saturated 5-, 6-, or 7-membered heterocyclic ring including pyridinium containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with one group selected from carboxy, amino, nitro, cyano, lower alkyl which is unsubstituted or substituted by fluoro, lower alkoxy, hydroxy, halogen, —COR$^6$, —C(R$^5$R$^6$)CO$_2$R$^7$, —C(R$^5$R$^6$)CONR$^5$R$^8$, —CONR$^5$R$^6$, —N(R$^6$)COOR$^{10}$, R$^6$OCO— or R$^6$COO— where $R^5$ and $R^6$ are hydrogen or lower alkyl; $R^7$ is hydrogen or a carboxylic acid protecting group; $R^8$ is hydrogen, lower alkyl or phenyl which is unsubstituted or substituted with at least one halogen, hydroxy, amino, lower alkyl or lower alkoxy; $R^{10}$ is a carboxylic acid protecting group;

Q is —CHR—, —CO— or —SO$_2$—;

R is hydrogen or lower alkyl;

$R^3$ is hydroxy, —O— when $R^2$ is a quaternary heterocyclic ring or a quaternary heterocyclyl lower alkyl, lower alkoxy, —OM and M represents an alkali metal;

m is 0 or 1;

n is 0, 1 or 2;

x is CH or N as well as esters thereof which are readily hydrolyzable in vivo, pharmaceutically acceptable salts of said compounds and hydrates of the compounds of formula I and of their esters and salts, and a pharmaceutically acceptable carrier.

151. The method of claim 150, wherein X is CH.

152. The method of claim 151, wherein $R^2$ is a heterocycle ring which is substituted by lower alkyl which is unsubstituted or —C(R$^5$R$^6$)CONR$^5$R$^6$.

153. The method of claim 152, wherein $R^2$ is a heterocycle ring which is substituted by lower alkyl which is unsubstituted.

154. The method of claim 153, wherein $R^1$ is hydrogen.

155. The method of claim 154, (6R, 7S)-7-[(Z)-2-(2-Amino-thiazol-4-yl)-2-hydroxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate.

156. The method of claim 154, (6R, 7S)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

157. The method of claim 154, (6R, 7S)-7-[(Z)-2-(2-Amino-thiazol-4-yl)-2-hydroxyimino-acetylamino]-3-[(E)-1-(1-methyl-pyridin-1-ium-4-yl)-2-oxo-pyrrolidin-3-ylidenemethyl]-8-oxo-1-aza-bicyclo[4.2.0]oct-2-ene-2-carboxylate.

158. The method of claim 153, wherein $R^1$ is lower alkyl which is unsubstituted.

159. The method of claim 158, (6R, 7S)-7-[(Z)-2-(2-Amino-thiazol-4-yl)-2-methoxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

160. The method of claim 153, wherein $R^1$ is cycloalkyl.

161. The method of claim 160, wherein $R^1$ is cyclopentyl.

162. The method of claim 161, (6R, 7S)-7-[(Z)-2-(2-Amino-thiazol-4-yl)-2-cyclopentyloxyimino-acetylamino]-3-[(E)-1-(1-methyl-pyridin-1-ium-2-yl)-2-oxo-pyrrolidin-3-ylidenemethyl]-8-oxo-1-aza-bicyclo[4.2.0]oct-2-ene-2-carboxylate.

163. The method of claim 161, (6R, 7S)-7-[(Z)-2-(2-Amino-thiazol-4-yl)-2-cyclopentyloxyimino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

164. The method of claim 153, wherein $R^1$ is —COR$^4$.

165. The method of claim 164, wherein $R^4$ is hydrogen.

166. The method of claim 165, (6R, 7S)-7-[(Z)-2-Acetoxyimino-2-(2-amino-thiazol-4-yl)-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

167. The method of claim 152, wherein $R^2$ is a heterocycle ring which is substituted by —$C(R^5R^6)CONR^5R^6$.

168. The method of claim 167, wherein each of $R^5$, $R^6$, and $R^8$ are hydrogen.

169. The method of claim 168, (6R, 7S)-7-[(Z)-2-Acetoxyimino-2-(2-amino-thiazolo-4-yl)-acetylamino]-3-[(E)-1-(1-carbamoylmethyl-pyridin-1-ium-3-yl)-2-oxo-pyrrolidin-3-ylidenemethyl]-8-oxo-1-aza-bicyclo[4.2.0]oct-2-ene-2-carboxylate.

170. The method of claim 150, wherein X is N.

171. The method of claim 170, wherein $R^2$ is a heterocycle ring which is substituted by lower alkyl which is unsubstituted or —$C(R^5R^6)CONR^5R^6$.

172. The method of claim 171, wherein R2 is a heterocycle ring which is substituted by lower alkyl which is unsubstituted.

173. The method of claim 172, wherein R1 is hydrogen.

174. The method of claim 173, (6R, 7S)-7-[(Z)-2-(5-Amino-[1,2,4]thiadiazol-3-yl)-hydroxyimino-acetylamino]-3-[(E)-1-(1-methyl-pyridin-1-ium-3-yl)-2-oxo-pyrrolidin-3-ylidenemethyl]-8-oxo-1-aza-bicyclo[4.2.0]oct-2-ene-2-carboxylate.

175. The method of claim 172, wherein R1 is cycloalkyl.

176. The method of claim 175, wherein R1 is cyclopentyl.

177. The method of claim 176, (6R, 7S)-7-[(Z)-2-(5-Amino-[1,2,4]thiadiazol-3-yl)-cyclopentyloximino-acetylamino]-3-[(E)-1-(1-methyl-pyridin-1-ium-3-yl)-2-oxo-pyrroliden-3-ylidenemethyl]-8-oxo-1-aza-bicyclo[4.2.0]oct-2-ene-2-carboxylate.

\* \* \* \* \*